US009119837B2

(12) United States Patent
Hammock et al.

(10) Patent No.: US 9,119,837 B2
(45) Date of Patent: *Sep. 1, 2015

(54) USE OF SEH INHIBITORS AS ANALGESICS

(75) Inventors: Bruce D. Hammock, Davis, CA (US); Ahmet Bora Inceoglu, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 1356 days.

This patent is subject to a terminal disclaimer.

(21) Appl. No.: 12/063,653

(22) PCT Filed: Aug. 18, 2006

(86) PCT No.: PCT/US2006/032595
§ 371 (c)(1),
(2), (4) Date: Apr. 15, 2008

(87) PCT Pub. No.: WO2007/022509
PCT Pub. Date: Feb. 22, 2007

(65) Prior Publication Data
US 2008/0249055 A1 Oct. 9, 2008

Related U.S. Application Data

(60) Provisional application No. 60/709,741, filed on Aug. 19, 2005.

(51) Int. Cl.
*A61K 31/17* (2006.01)
*A61K 31/16* (2006.01)
*A61K 31/336* (2006.01)
*A61P 25/02* (2006.01)
*A61P 25/04* (2006.01)
*A61K 31/335* (2006.01)

(52) U.S. Cl.
CPC .................................... *A61K 31/335* (2013.01)

(58) Field of Classification Search
CPC ............ A61K 31/427; A61K 31/4439; A61K 31/4465; A61K 31/335; A61K 45/06; A61K 2300/00
USPC .................. 514/475, 588, 613, 546, 342, 354
See application file for complete search history.

(56) References Cited

U.S. PATENT DOCUMENTS

| 4,310,525 | A | 1/1982 | Nelson |
| 5,505,949 | A | 4/1996 | Benitez |
| 5,955,496 | A | 9/1999 | Hammock et al. |
| 6,150,415 | A | 11/2000 | Hammock et al. |
| 6,174,695 | B1 | 1/2001 | Hammock et al. |
| 6,531,506 | B1 * | 3/2003 | Kroetz et al. ............... 514/475 |
| 6,831,082 | B2 | 12/2004 | Ingraham et al. |
| 7,396,831 | B2 * | 7/2008 | Doherty et al. ............... 514/247 |
| 2001/0016584 | A1 | 8/2001 | Camborde et al. |
| 2002/0077355 | A1 | 6/2002 | Liao et al. |
| 2004/0092567 | A1 | 5/2004 | Ingraham et al. |
| 2006/0178347 | A1 * | 8/2006 | Hammock et al. ............... 514/165 |

FOREIGN PATENT DOCUMENTS

| WO | WO 99/54282 | 10/1999 |
| WO | WO 00/23060 | 4/2000 |

OTHER PUBLICATIONS

Merkel et al. (A695, Abstract, Proc of the 2010 Annual Meeting of the Am. Soc. Anesthesiologists, 'Sex Differences in Cardioprotection in the sEH/EET signaling Pathway, p1).*
Morisseau et al. (Biochem Pharmacology, 63, 2002, 1599-1608.*
Jung et al. (Hypertension, 2005, 45, 759-765).*
Boulton (Clinical Diabetes, Jan. 2005, 23, 1, p. 9-15).*
Suyama (Brain Research, 1010, 2004, 144-150).*
Jain (Clinical Summary 2000).*
Quintao (Anesth Analg 2005, 101, 1763-9).*
Gallazi (JAOA, 4, 105, 9, 2005, p. s12-s19).*
Node, K., et al., "Anti-inflammatory Properties of Cytochrome P450 Epoxygenase-Derived Eicosanoids," Science, vol. 285, pp. 1276-1279 (Aug. 20, 1999).
Ahlgren et al, "Mechanical Hyperalgesia in Streptozotocin-Diabetic Rats", Neuroscience, vol. 52, No. 4, pp. 1049-1055, 1993.
Aley et al., "Rapid Onset Pain Induced by Intravenous Streptozotocin in the Rat", The Journal of Pain, vol. 2., No. 3 (Jun. 2001),: pp. 146-150.
Arnér et al., "Lack of analgesic effect of opioids on neuropathic and idiopathic forms of pain", Pain, 33 (1988) 11-23.
Basbaum, Allan I. et al., "Cellular and Molecular Mechanisms of Pain", Cell 139, Oct. 16, 2009, 267.
Basbaum, Allan I. et al., "Pain" Current Biology, vol. 9 No. 12, (1999).
Courteix et al., "Study of the sensitivity of the diabetes-induced pain model in rats to a range of analgesics", Pain, 57 (1994) 153-160.
Dworkin, Robert H. et al. "Pharmacologic management of neuropathic pain: Evidence-based recommendations", Pain 132 (2007) 237-251.
Inceoglu, Bora et al., "Inhibition of soluble epoxide hydrolase reduces LPS-induced thermal hyperalgesia and mechanical allodynia in a rat model of inflammatory pain", ScienceDirect, Life Sciences 79 (2006) 2311-2319.
Inceoglu, Bora et al., "Soluble epoxide hydrolase and epoxyeicosatrienoic acids modulate two distinct analgesic pathways", PNAS, Dec. 2, 2008, vol. 105, No. 48, 18901-18906.
Inceoglu, Bora et al., "Soluble epoxide hydrolase inhibition reveals novel biological functions of epoxyeicosatrienoic acids (EETs)", Prostaglandins Other Lipid Mediat, (Jan. 2007); 82 (1-4): 42-49.
Julius, David et al., "Molecular mechanisms of nociception", Nature, vol. 413, Sep. 13, 2001.
Kloke, et al., "Anti-depressants and anti-convulsants for the treatment of neuropathic pain syndromes in cancer patients," Onkologie (1991) 14(1):40-3.
Liu, Jun-Yan et al., "Inhibition of soluble epoxide hydrolase enhances the anti-inflammatory effects of aspirin and 5-lipoxygenase activation protein inhibitor in a murine model", Biochemical Pharmacology, 79 (2010) 880-887.
Melinkova, Irena, "Pain Market", Nature Reviews, vol. 9, Aug. 2010, 589.

(Continued)

Primary Examiner — Uma Ramachandran
(74) Attorney, Agent, or Firm — DLA Piper LLP (US)

(57) ABSTRACT

The present invention provides methods and compositions for relieving pain and itching, of promoting wound healing, of reducing sickness behavior and of reducing inflammatory bowel disease or acne lesions in a subject by the topical administration of an inhibitor of soluble epoxide hydrolase, or of a cis-epoxyeicosatrienoic acid ("EET"), or by both.

11 Claims, 6 Drawing Sheets

(56) References Cited

OTHER PUBLICATIONS

Omoigui, Sota, MD, "The biochemical origin of pain—Proposing a new law of pain: The origin of all pain is inflammation and the inflammatory response. Part 1 of 3—A unifying law of pain", *Medical Hypothese* (2007) 69, 70-82.

Omoigui, Sota, MD, "The Biochemical Origin of Pain: The origin of all Pain is Inflammation and the Inflammatory Response. Part 2 of 3—Inflammatory Profile of Pain Syndromes", *Med Hypotheses* (2007) 69(6) 1169-1178.

Presley, et al., "Novel Approaches to the Treatment of Neuropathic Pain" West J Med (1992) 157(5):564.

Schmelzer et al., "Enhancement of anitnociception by coadministration of nonsterioidal anti-inflammatory drugs and soluble epoxide hydrolase inhibitors", PNAS, Sep. 12, 2006, vol. 103, No. 37, 13646-13651.

Snider, William D. et al., "Tackling Pain at the Source: New Ideas about Nociceptors", Neuron, vol. 20, 629-632, Apr. 1998.

Xu, Qinghao et al., "A brief comparison of the pathophysiology of inflammatory versus neuropathic pain", *Current Opinion in Anesthesiology* 2011, 24:400-407.

Smith et al.: "*Attenuation of tobacco smoke-induced lung inflammation by treatment with a soluble epoxide hydrolase inhibitor*"; Proc Natl Acad Scl USA, 102(6), pp. 2186-2191, Feb. 8, 2005.

* cited by examiner

USE OF SEH INHIBITORS AS ANALGESICS

CROSS-REFERENCES TO RELATED APPLICATIONS

This application is a U.S. National Stage Application of PCT/US2006/032595 filed Aug. 18, 2006, which claims the benefit of and priority from U.S. Provisional Application No. 60/709,741, filed Aug. 19, 2005, the contents of which are incorporated by reference.

STATEMENT AS TO RIGHTS TO INVENTIONS MADE UNDER FEDERALLY SPONSORED RESEARCH AND DEVELOPMENT

This invention was made with Government support under Grant No. R37 ES 02710 awarded by the National Institutes of Health. The Government has certain rights in this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Tissue injury results in the release of a diverse group of inflammatory mediators that sensitize nociceptors and spinal nociceptive neurons to mechanical and thermal stimuli, leading to heightened pain transmission. Local, systemic, or neurogenic release of inflammatory mediators include K+, neuropeptides, such as substance P, peptides such as bradykinin, cytokines, monoamines, and ATP, which activate or sensitize peripheral nociceptors. Furthermore, peripheral sensitization of nociceptors can, in turn, lead to central sensitization in the spinal cord, producing secondary hyperalgesia and allodynia through processes that include activation of NMDA.

Pain is currently considered to fall into three categories: nociceptive pain, activated by noxious stimuli on specialized receptors called nociceptors, inflammatory pain, in which damage to tissue causes release of inflammatory mediators, some of which directly activate nociceptors and others of which act to sensitive the somatosensory nervous system until the tissue heals, and neuropathic pain, in which damage or malfunction of peripheral or central nerves creates spontaneous pain with no protective or reparative role. See, Scholz and Woolf, Nature Neuroscience (Supp.) 5:1062-1067 (2002); Julius and Basbaum, Nature 413:203-210 (2001).

Long chain fatty acids, prominently arachidonic acid ("AA"), are molecules that lie at a pivotal point of important inflammatory cascades that result in peripheral sensitization of nociceptors. AA release activates two classes of enzymes: the cyclooxygenases (COX) and the lipoxygenases, which lead to the production of pro-inflammatory mediators including prostaglandins (PG) and leukotrienes. These enzymes have been the focus of intense research during the last decades, and inhibitors of these enzymes are major therapeutic agents for inflammatory pain. Another branch of the arachidonate cascade is the cytochrome P450-catalyzed conversion of AA and linoleic acid (LA). to a conspicuous group of metabolites including epoxyeicosatrienoic acid (EET), hydroxyeicosatrienoic acids (HETEs) and epoxyoctadecenoic acids (EpOMEs). Among these metabolites, EET is the putative endothelium-derived hyperpolarization factor, which exerts anti-inflammatory and antihypertensive effects in the cardiovascular system. EETs and EpOMEs are short-lived AA and LA metabolites that are converted by the enzyme soluble epoxide hydrolase ("sEH") to pro-inflammatory dihydroeicosatrienoic acids (DHETs) and dihydroxyoctadecenoic acids (DiHOMEs), respectively. Inhibition of sEH increases detectable concentrations of EETs, decreasing blood pressure only under hypertensive conditions and reducing vascular inflammatory responses.

It would be useful to have additional agents which can be used for pain relief, particularly as topical agents.

BRIEF SUMMARY OF THE INVENTION

The present invention provide methods and topical compositions for reducing pain and itch associated with a variety of conditions. In a first set of embodiments, the invention provides methods for relieving pain or itch in a subject. The methods comprises topically administering to said subject an effective amount of an inhibitor of soluble epoxide hydrolase ("sEH"), thereby relieving pain or itch in the subject. In some embodiments, the pain relieved is nociceptive pain. In some embodiments, the pain relieved is inflammatory pain. In some embodiments, the pain relieved is neuropathic pain. In some embodiments, the pain is from arthritis. In some embodiments, the pain is from post-herpetic neuralgia. In some embodiments, the method further comprises topically administering an epoxide of a polyunsaturated fatty acid. In some embodiments, the epoxide is a cis-epoxyeicosatrienoic acid ("EET"). In some embodiments, the EET is selected from the group consisting of 5,6-EET, 14,15-EET, 8,9-EET, and 11,12-EET. In some embodiments, the subject does not have hypertension, or is not being treated for hypertension with an inhibitor of sEH. In some embodiments, the inhibitor of sEH is an isolated nucleic acid which inhibits expression of a gene encoding soluble epoxide hydrolase ("sEH"). In some embodiments, the inhibitor of sEH is administered to an area of skin one hour or less before a dermatological procedure or cosmetic surgery on said area of skin to relieve pain associated with said procedure or surgery. In some embodiments, the itch is due to pruritus. In some embodiments, the itch is due to an insect bite, to contact with urushiol, or to contact with an irritant chemical. In some embodiments, the pain or itch is due to a hemorrhoid. In some embodiments, the pain or itch is due to visceral pain and said topical administration is by a suppository comprising said inhibitor of sEHI.

In a further group of embodiments, the invention provides compositions comprising an inhibitor of soluble epoxide hydrolase ("sEH") in a cream, gel, oil, lotion, balm, ointment, suppository or topical spray. In some embodiments, the cream, gel, oil, lotion, balm, ointment, suppository or topical spray has a lipid base. In some embodiments, the composition further comprises an epoxide of a polyunsaturated fatty acid. In some embodiments, the epoxide of a polyunsaturated fatty acid is a cis-epoxyeicosatrienoic acid ("EET"). In some embodiments, the EET is selected from the group consisting of 5,6-EET, 14,15-EET, 8,9-EET, and 11,12-EET. In some embodiments, the inhibitor of sEH is an isolated nucleic acid which inhibits expression of a gene encoding soluble epoxide hydrolase ("sEH").

In yet a further group of embodiments, the invention provides methods of reducing sickness behavior in a subject. The methods comprises topically administering to said subject an effective amount of an inhibitor of soluble epoxide hydrolase ("sEH"), thereby reducing sickness behavior in the subject. In some embodiments, the method further comprises topically administering an epoxide of a polyunsaturated fatty acid. In some embodiments, the epoxide is a cis-epoxyeicosatrienoic acid ("EET"). In some embodiments, the EET is selected from the group consisting of 14,15-EET, 8,9-EET, and 11,12-EET. In some embodiments, the inhibitor of sEH is an isolated nucleic acid which inhibits expression of a gene encoding soluble epoxide hydrolase ("sEH"). In some embodiments, the subject does not have hypertension, or is not being treated for hypertension with an inhibitor of sEH.

In still a further group of embodiments, the invention provides methods of promoting wound healing in a subject. The methods comprise topically administering to the wound an effective amount of an inhibitor of soluble epoxide hydrolase ("sEH"), thereby promoting wound healing in the subject. In some embodiments, the methods further comprise topically administering an epoxide of a polyunsaturated fatty acid. In some embodiments, the epoxide is a cis-epoxyeicosatrienoic acid ("EET"). In some embodiments, the inhibitor of sEH is an isolated nucleic acid which inhibits expression of a gene encoding soluble epoxide hydrolase ("sEH").

In a further group of embodiments, the invention provides methods of relieving pain or itch or of reducing the size of improving appearance of an acne lesion in a subject, said method comprising topically administering to said subject a composition comprising an effective amount of a cis-epoxyeicosatrienoic acid ("EET") selected from 5,6-EET, 8,9-EET, 14,15-EET, or a combination thereof, thereby relieving pain or itch or improving the appearance of said acne lesion in said subject, provided that said composition does not also comprise an effective amount of 11,12-EET. In some embodiments, the pain or itch is due to pruritus, a hemorrhoid, a burn, post-herpetic neuralgia, arthritis, or a dermatological procedure.

In a further group of embodiments, the invention provides methods of reducing the size or improving the appearance of acne lesions in a subject. The methods comprise topically administering to the acne lesion an effective amount of an inhibitor of soluble epoxide hydrolase ("sEH"), whereby administration of the inhibitor reduces the size or improves the appearance of the acne lesion. In some embodiments, the methods further comprise topically administering to said lesion an epoxide of a polyunsaturated fatty acid. In some embodiments, the epoxide is a cis-epoxyeicosatrienoic acid ("EET"). In some embodiments, the inhibitor of sEH is an isolated nucleic acid which inhibits expression of a gene encoding soluble epoxide hydrolase ("sEH").

DETAILED DESCRIPTION OF THE INVENTION

Introduction

Figure 1:
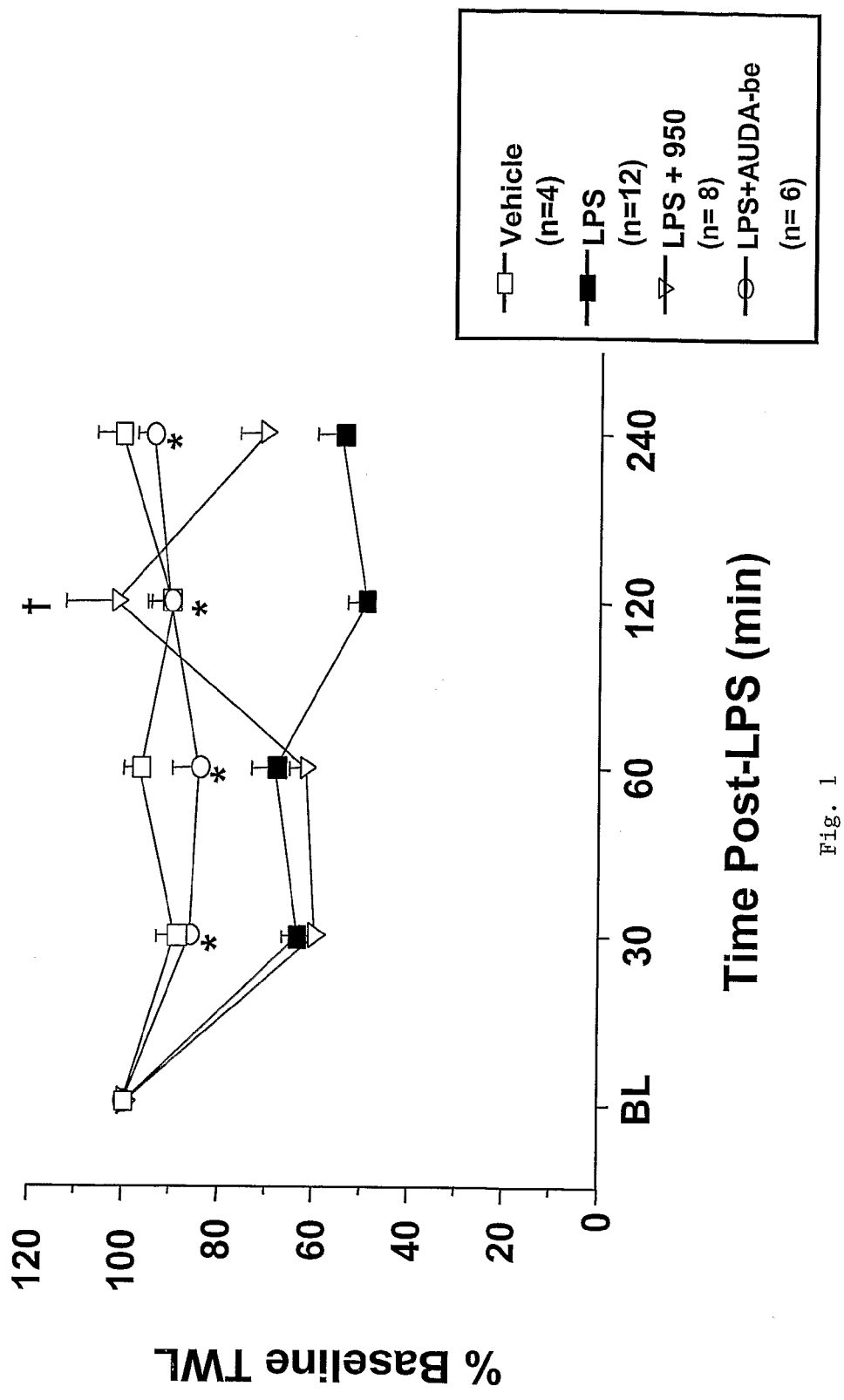
FIG. 1 shows that two sEH inhibitors block lipopolysaccharide ("LPS")-induced thermal hyperalgesia. AUDA-butyl ester ("be") and 950 are two sEH inhibitors. X axis is time after administration of the agents. Y axis is percent thermal withdrawal latency ("TWL"). Hollow boxes: vehicle cream (Vanicream®). Filled boxes: LPS (10 μg) in the cream vehicle. Circles: AUDA-be (50 mg/kg) and LPS (10 μg). Triangles: compound 950 (50 mg/kg) and LPS (10 μg). Asterisks and cross denote statistically significant results. In this and the Figures below, the agents are administered in the same vehicle cream.
Figure 2:
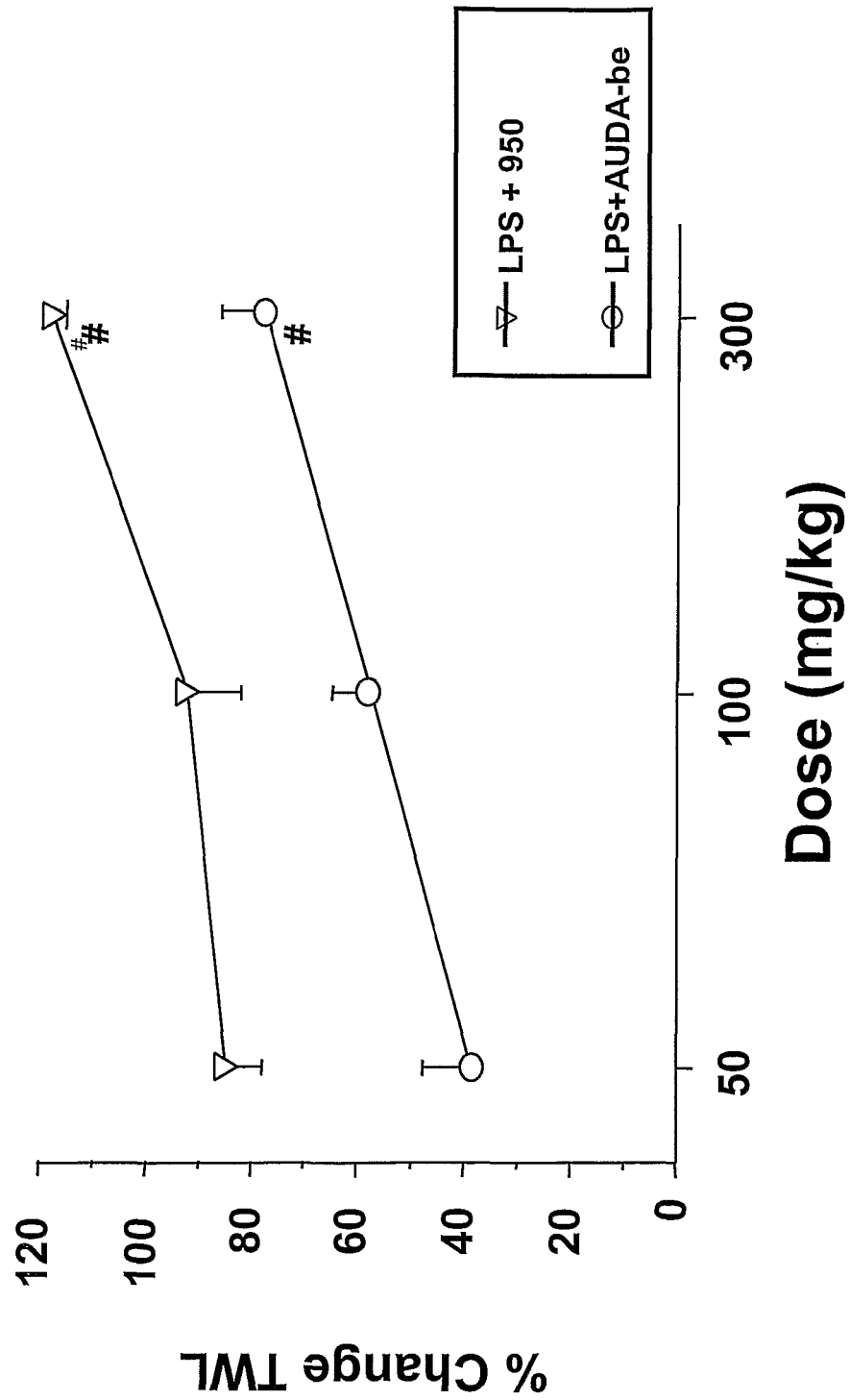
FIG. 2 shows that two sEH inhibitors block LPS-induced thermal hyperalgesia in a dose dependent way. AUDA-be and 950 are two sEH inhibitors. X axis shows in mg/kg. Y axis is percent thermal withdrawal latency ("TWL"). Circles: AUDA-be (50 mg/kg)+LPS (10 μg). Triangles: compound 950 (50 mg/kg)+LPS (10 μg).

The systemic administration of inhibitors of the enzyme known as "soluble epoxide hydrolase", or "sEH", has recently been found to have a number of beneficial applications, such as for reducing hypertension. Surprisingly, it has now been found that topical administration of sEH inhibitors (or "sEHI") is also useful, and for entirely different purposes.

In studies using two different animal models for three different types of pain, animals to whom exemplar sEH inhibitors ("sEHI") were administered topically showed reduced sensitivity to pain stimuli. The response to pain stimuli was further reduced by including cis-epoxyeicosatrienoic acids ("EETs") in the topical preparation. One set of studies showed that administration of exemplar sEHIs reduced thermal hyperalgesia. A second set of studies showed a reduced response to mechanical allodynia induced by bacterial lipopolysaccharide ("LPS"). A third set showed that response to neurogenic pain induced by capsaicin, the ingredient that is perceived as "heat in "hot" peppers, was reduced upon topical application of a cream containing sEHI and enhanced by the presence of EETs.

The results indicate that topical administration of sEHI reduces these three distinct forms of pain, and that the effect of sEHI in pain relief can be enhanced by including epoxides of polyunsaturated fatty acids, such as EETs, in the topical formulation. Based on the results of the studies underlying the present invention, topical administration of sEHI is expected to ease itching, irritation, burning or pain in dermatoses, including nonspecific pruritus. For example, topical administration of sEHI is expected to alleviate pain in fingers or toes from osteoarthritis or rheumatic arthritis, as well as pain from sunburn or mild burns. Indeed, topical administration of sEHI is expected to reduce radiation irritation and burns generally (including that caused by UV or ionizing radiation), chemical burns, thermal burns, reddening of the skin, and chemically induced lesions.

In an important set of uses, it is expected that topical administration of sEHI will reduce neuralgia, pain caused by trauma or irritation to peripheral nerves near the surface of the skin. In particular, it is expected be useful in relieving post-herpetic neuralgia, such as that from shingles, and pain in the extremities from diabetic neuropathy.

In studies, we have also found that topical administration of sEHI relieves itching. Topical administration of sEHI is therefore expected to help relieve the itching caused by insect bites, as well itching due to an allergic reaction to contact with urushiol. Urushiol is a hydrophobic oil found in certain plants, particularly those of the genus *Toxicodendron*, such as poison ivy, poison oak, and poison sumac. Urushiol-induced contact dermatitis is characterized in part by intense itching in sensitive individuals. As noted, topical application of sEHI reduces the itching associated with urushiol contact. Given the effect of sEHI on relieving the itch from contact with urushiol, it is expected that topical application sEHI, EETs, or both, will also relieve itching caused by other types of contact dermatitis, such as nickel allergy, or from contact with irritating or industrial chemicals. More generally, it is expected that sEHI, EETs, or both, will prove useful in relieving pruritus, including not only contact dermatitis but also atopic dermatitis and xerotic eczema, as well as lichen simplex chronicus, hives, chicken pox, and impetigo.

We have also developed information indicating that topical application of sEHI, EETs, or both, is useful in relieving pain associated with anal hemorrhoids. Further, the anti-itch properties of the sEHI and EETs is useful in reducing the itching associated with anal pruritus.

Irritable bowel syndrome stems in part from visceral pain. Given the effects of sEHI and EETs in relieving pain, it is believed that topical administration to the bowel by use of suppositories releasing the sEHI, EETs, or both, will relieve irritable bowel syndrome.

Topical administration of sEHI, EETs, or both, can also be used prophylatically to reduce the pain and irritation that would otherwise be experienced during and after minor cosmetic surgery, such as chemical peels, removal of warts, minor skin lesions, or superficial cancers, as well as other dermatologic procedures. Preferably, the sEHI is applied to the skin on and around which the procedure is to be performed between ten minutes and one hour before the procedure is to be performed, with ten to fifteen minutes in advance being preferred. Of course, the sEHI, EETs, or both can also be administered after the procedure to reduce any pain or discomfort resulting from the procedure, whether or not one or both were administered before the procedure.

As noted, capsaicin (CAP), the active constituent found in various members of the pepper family, induces an acute neurogenic inflammatory response when applied topically to skin. CAP is a highly selective pain-producing substance that selectively stimulates nociceptive and thermal-sensitive nerve endings in tissues by acting on a specific membrane receptor. The mode of action of capsaicin therefore differs significantly from phorbol myristate acetate (PMA)-induced inflammation. By comparison, PMA elicits its pro-inflammatory effects through cellular activation of specific immune cells, such as macrophages and neutrophils. Consequently, the pain response to PMA develops more slowly than the immediate, but transient, pain response to capsaicin.

The studies underlying the invention show that the methods and compositions of the invention block the nociceptive (CAP-induced) inflammatory pathway, thereby providing a method for inhibiting neurogenic inflammation. These in vivo studies suggest sEHIs or epoxides of polyunsaturated fatty acids might be acting through the cannabinoid/vanilloid system. The ability to relieve capsaicin induced pain suggests there is an action on transient receptor potential channels.

The methods of the invention contemplate that the patient will rub or spread on the affected area a cream, gel, oil, balm, lotion or ointment containing an sEHI or will spray the affected area with the sEHI. The composition (e.g., the cream, gel, oil, balm, ointment, or spray) may further comprise epoxides of polyunsaturated fatty acids, such as one or more EETs. In some embodiments, the composition contains low concentrations of sEHI or EETs for use as over the counter medications such as anti-itch and anti-pain medications intended to relieve the itching of poison ivy or the pain of sunburns and the like. In other embodiments, where the intent is to alleviate more serious pain, as in more extensive or deeper burns, or for use to relieve pain during or from a dermatological procedure or cosmetic surgery, higher concentrations of sEHI or EETs, or of both, may be used. Such procedures include mole removal, removal of surface skin cancers and the like.

Some of the past disclosures on the use of sEHI for treatment of various conditions have mentioned the topical administration of the agents. The topical administration referenced in those disclosures, such as the treatment of hypertension, was however as a transdermal application to deliver sEHI or EETs or both into the systemic circulation to, for example, cause a reduction in hypertension. In contrast, in the methods and compositions of the present invention, any introduction of the agents into the systemic circulation is incidental. Instead, what is desired is achieving a high local concentration of the agents in the skin or the area under it, such as the joint. For example, the application of topical formulations of sEHI, with or without an EET, to arthritic fingers or toes is not expected to have a significant impact on levels of sEH activity or of EETs elsewhere in the body. Studies with other agents intended for relief of pain, such as non-steroidal anti-inflammatory drugs (NSAIDs) like ibuprofen, indicate that, when such compositions are applied topically over an area, the muscles and joints under the area show relatively high concentrations of the agent with relatively limited levels of the agent in the blood.

Many if not all of the indications contemplated by prior uses for sEHI or EETs are chronic conditions in which effective treatment calls for the use of sEHI or EETs over an extended period, if not over the remainder of the patient's life. In contrast, many of the uses contemplated by the present invention are of short duration, such as the itch associated with an insect bite or even that associated with contact with poison ivy or chemical irritants.

It is understood that there may be some incidental entry of the agents into the systemic circulation, but this is not believed to play a significant role in the relief of pain and is not considered important to the practice of the methods of the invention. For example, in the instance in which a patient's shoulders and back are sunburned, applying sEHI or EETs, or both, topically over such a large affected area may well permit incidental entrance of the agents into the systemic circulation in amounts sufficient to affect sEH activity (in the case of administering an sEHI) or to boost systemic EET levels (if EETs are administered). It is expected, however, that the agents will only be employed topically over wide areas for the duration of pain induced by a particular cause, such as a burn, rather than as a chronic administration to the circulation. It is noted in passing that application of the agents over larger body areas, as may be useful in treatment of sunburns and the like, may conveniently be done by means of a topical spray comprising the sEHI or EETs or both.

In some embodiments, it may indeed be undesirable that the person being treated be contacted with sEHIs systemically. In such instances, it may be desirable to administer the sEHI as a "soft drug." A soft drug is an analog (often isosteric or isoelectronic, or both) of a compound designed to be metabolized into an inactive form after it exerts the desired effect. Typically, such drugs are administered locally, where they exert the desired effect, and are metabolized into an inactive form as they distribute away from the desired site of action. For example, soft drug forms of sEHI are esters that can be degraded by endogenous esterases. Typically, for sEHI that have carbonyl groups, the ester is created near the carbonyl. The soft drug form of the sEHI can be introduced into a carrier, such as a cream or ointment, so that the cream or ointment introduces the agent locally to desired area. The action of the endogenous esterase can then degrade the sEHI into an inactive form before it enters the systemic circulation, or while it is circulating, diminishing or avoiding systemic effect of the agent. Formulation of soft drugs is well known in the art.

The studies underlying the invention showed not only reduction of pain but also a diminishment of "sickness behavior." Little is known about the basis of sickness behavior. It is hypothesized that cytokine mediated mechanisms, such as interleukin-1 (IL-1), interleukin-6 (IL-6), and tumor necrosis factor α (TNFα) are involved (Larson S. J. and Dunn A. J., "Behavioral Effects of Cytokines," Brain, Behavior, and Immunity 15:371-387 (2001)). Sickness behavior has very clear symptoms. Illness causes mammals to lose interest in their environment, to exhibit an increase in sleep, and to decrease food intake, social interaction, mobility, exploration, and sexual behavior. Mammals also exhibit a decrease in cognitive function, as well as various psychological effects such as a loss of response to hedonic stimuli. Sickness behavior is an advantageous defense mechanism. Hart argued that "the behavior of a sick individual is not a maladaptive and undesirable effect of illness but rather a highly organized strategy that is at times critical to the survival of the individual if it were living in the wild state" (Hart, B. L., "Biological basis of the behavior of sick animals," Neurosci. Biobehav. Rev. 12, 123-137 (1988)). Animals treated with sEH inhibitors, EETs or a combination of the two showed a clear decrease in sickness behavior.

Ameliorating the sickness behavior has far more impact than just feeling good. Sickness behavior is accompanied with physiological and chemical changes in mammals. Shifting the metabolite pool towards naturally occurring healing molecules not only progresses the chemical condition of the animal towards a healthy state, but is expected to improve the animal's psychological state.

The effects noted with respect to reducing pain also lead to the expectation that the compositions can be used in methods to promote wound healing. In these methods, the compositions of sEHI, of epoxides of polyunsaturated fatty acids, such as EETs, or both, are applied to a wound to promote its healing. It is also expected that the agents can be topically applied to the surface of the bowel in suppositories to reduce inflammatory bowel disease or hemorrhoids. Further, because of the effect on neurogenic inflammation, it is expected that topical application of the compositions of the invention will be effective in improving the appearance of the pimples and skin lesions associated with acne.

As noted, it has previously been found that sEHI can be used to treat hypertension. Hypertension can, of course, be treated with agents other than EETs and sEHI. The present invention, however, indicates that treatment with EETs or sEHI will have an analgesic effect and is therefore to be preferred over the use of other anti-hypertensive agents. Similarly, while inflammation can be treated with agents other than EETs and sEHI, treatment of inflammation with sEHI, EETs, or both, is therefore to be preferred over the use of other anti-inflammatory agents.

In some preferred embodiments, the person being treated systemically with EETs, sEHI, or both, to relieve pain does not have hypertension, if the person has hypertension, has not been treated for this condition with an sEHI or EET. Further, in some preferred embodiments, the person being treated to relieve pain does not have inflammation other than any inflammation associated with the source of the pain or, if he or she has other inflammation, has not been treated for this condition with an sEH inhibitor or an EET. In some preferred embodiments, the person has inflammation but is being treated for that inflammation by an anti-inflammatory agent, such as a steroid, that is not an inhibitor of sEH. Whether or not any particular anti-inflammatory agent or anti-hypertensive agent is also an sEH inhibitor can be readily determined by standard assays for inhibition of sEH activity, such as those taught in U.S. Pat. No. 5,955,496.

In some preferred embodiments, the patient to be treated topically to relieve pain does not also have a disease or condition caused by an autoimmune disease or a disorder associated with a T-lymphocyte mediated immune function autoimmune response. In some embodiments, the patient does not also have a pathological condition selected from type 1 or type 2 diabetes, insulin resistance syndrome, atherosclerosis, coronary artery disease, angina, ischemia, ischemic stroke, Raynaud's disease, or renal disease. In some embodiments, the patient is not a person with diabetes mellitus whose blood pressure is 130/80 or less, a person with metabolic syndrome whose blood pressure is less than 130/85, a person with a triglyceride level over 215 mg/dL, or a person with a cholesterol level over 200 mg/dL or is a person with one or more of these conditions who is not taking an inhibitor of sEH. In some embodiments, the patient does not have an obstructive pulmonary disease, an interstitial lung disease, or asthma. In some embodiments, the patient does not have cardiomyopathy, cardiac hypertrophy, or a cardiac arrhythmia, or is not being treated for these conditions with an sEHI or EET. In some embodiments, the patient has not had a stroke. In some embodiments, the patient does not have glaucoma or dry eye syndrome or is not being treated for glaucoma or dry eye syndrome with an sEHI or an EET. In some embodiments, the patient is not also being treated with an inhibitor of one or more enzymes selected from the group consisting of cyclo-oxygenase ("COX")-1, COX-2, and 5-lipoxygenase ("5-LOX"). In some embodiments, the patient is not concerned with reducing the formation of adipocytes in the area to which the sEHI or EETs or both is to be applied.

Medicaments of EETs can be made which can be administered by themselves or in conjunction with one or more sEH inhibitors, or a medicament containing one or more sEH inhibitors can optionally contain one or more EETs. The EETs can be administered alone, or concurrently with a sEH inhibitor or following administration of a sEH inhibitor. It is understood that, like all drugs, inhibitors have half lives defined by the rate at which they are metabolized by or excreted from the body, and that the inhibitor will have a period following administration during which it will be present in amounts sufficient to be effective. If EETs administered after an sEH inhibitor are intended to be administered while the sEH inhibition is still in effect, therefore, it is desirable that the EETs be administered during the period during which the inhibitor will be present in amounts to be effective to delay hydrolysis of the EETs.

In some embodiments, the sEH inhibitor may be a nucleic acid, such as a small interfering RNA (siRNA) or a micro RNA (miRNA), which reduces expression of a gene encoding sEH in cells in or around the site from which the pain is experienced. The EETs may be administered in combination with such a nucleic acid. Typically, a study will determine the time following administration of the nucleic acid before a decrease is seen in levels of sEH. The EET or EETs will typically then be administered a time calculated to be after the activity of the nucleic acid has resulted in a decrease in sEH levels.

DEFINITIONS

Units, prefixes, and symbols are denoted in their Système International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety. Terms not defined herein have their ordinary meaning as understood by a person of skill in the art.

"cis-Epoxyeicosatrienoic acids" ("EETs") are biomediators synthesized by cytochrome P450 epoxygenases. As discussed further in a separate section below, while the use of unmodified EETs is the most preferred, derivatives of EETs, such as amides and esters (both natural and synthetic), EETs analogs, and EETs optical isomers can all be used in the methods of the invention, both in pure form and as mixtures of these forms. For convenience of reference, the term "EETs" as used herein refers to all of these forms unless otherwise required by context.

"Epoxide hydrolases" ("EH;" EC 3.3.2.3) are enzymes in the alpha beta hydrolase fold family that add water to 3 membered cyclic ethers termed epoxides.

"Soluble epoxide hydrolase" ("sEH") is an epoxide hydrolase which in endothelial and smooth muscle cells converts EETs to dihydroxy derivatives called dihydroxyeicosatrienoic acids ("DHETs"). The cloning and sequence of the murine sEH is set forth in Grant et al., J. Biol. Chem. 268(23): 17628-17633 (1993). The cloning, sequence, and accession numbers of the human sEH sequence are set forth in Beetham et al., Arch. Biochem. Biophys. 305(1):197-201 (1993). The amino acid sequence of human sEH is also set forth as SEQ ID NO:2 of U.S. Pat. No. 5,445,956; the nucleic acid sequence encoding the human sEH is set forth as nucleotides 42-1703 of SEQ ID NO:1 of that patent. The evolution and nomenclature of the gene is discussed in Beetham et al., DNA Cell Biol. 14(1):61-71 (1995). Soluble epoxide hydrolase represents a single highly conserved gene product with over 90% homology between rodent and human (Arand et al., FEBS Lett., 338:251-256 (1994)). Unless otherwise specified, as used herein, the terms "soluble epoxide hydrolase" and "sEH" refer to human sEH.

Unless otherwise specified, as used herein, the term "sEH inhibitor" (also abbreviated as "sEHI") refers to an inhibitor of human sEH. Preferably, the inhibitor does not also inhibit the activity of microsomal epoxide hydrolase by more than 25% at concentrations at which the inhibitor inhibits sEH by at least 50%, and more preferably does not inhibit mEH by more than 10% at that concentration. For convenience of reference, unless otherwise required by context, the term "sEH inhibitor" as used herein encompasses prodrugs which are metabolized to active inhibitors of sEH. Further for convenience of reference, and except as otherwise required by context, reference herein to a compound as an inhibitor of sEH includes reference to derivatives of that compound (such as an ester of that compound) that retain activity as an sEH inhibitor.

"Neurogenic inflammation" refers to a response evoked by neuropeptides released from primary afferent nerve terminals and by other secondarily released inflammatory mediators in response to.

"Anti-neurogenic inflammatory activity," as used herein, refers to activity inhibiting or controlling a neurogenic inflammatory response.

By "physiological conditions" is meant an extracellular milieu having conditions (e.g., temperature, pH, and osmolarity) which allows for the sustenance or growth of a cell of interest.

"Micro-RNA" ("miRNA") refers to small, noncoding RNAs of 18-25 nt in length that negatively regulate their complementary mRNAs at the posttranscriptional level in many eukaryotic organisms. See, e.g., Kurihara and Watanabe, Proc Natl Acad Sci USA 101(34):12753-12758 (2004). Micro-RNA's were first discovered in the roundworm *C. elegans* in the early 1990s and are now known in many species, including humans. As used herein, it refers to exogenously administered miRNA unless specifically noted or otherwise required by context.

Inhibitors of Soluble Epoxide Hydrolase

Scores of sEH inhibitors are known, of a variety of chemical structures. Derivatives in which the urea, carbamate, or amide pharmacophore (as used herein, "pharmacophore" refers to the section of the structure of a ligand that binds to the sEH) is covalently bound to both an adamantane and to a 12 carbon chain dodecane are particularly useful as sEH inhibitors. Derivatives that are metabolically stable are preferred, as they are expected to have greater activity in vivo. Selective and competitive inhibition of sEH in vitro by a variety of urea, carbamate, and amide derivatives is taught, for example, by Morisseau et al., Proc. Natl. Acad. Sci. U.S.A, 96:8849-8854 (1999), which provides substantial guidance on designing urea derivatives that inhibit the enzyme.

Derivatives of urea are transition state mimetics that form a preferred group of sEH inhibitors. Within this group, N,N'-dodecyl-cyclohexyl urea (DCU), is preferred as an inhibitor, while N-cyclohexyl-N'-dodecylurea (CDU) is particularly preferred. Some compounds, such as dicyclohexylcarbodiimide (a lipophilic diimide), can decompose to an active urea inhibitor such as DCU. Any particular urea derivative or other compound can be easily tested for its ability to inhibit sEH by standard assays, such as those discussed herein. The production and testing of urea and carbamate derivatives as sEH inhibitors is set forth in detail in, for example, Morisseau et al., Proc Natl Acad Sci (USA) 96:8849-8854 (1999).

N-Adamantyl-N'-dodecyl urea ("ADU") is both metabolically stable and has particularly high activity on sEH. (Both the 1- and the 2-admamantyl ureas have been tested and have about the same high activity as an inhibitor of sEH.) Thus, isomers of adamantyl dodecyl urea are preferred inhibitors. It is further expected that N,N'-dodecyl-cyclohexyl urea (DCU), and other inhibitors of sEH, and particularly dodecanoic acid ester derivatives of urea, are suitable for use in the methods of the invention. Preferred inhibitors include:

12-(3-Adamantan-1-yl-ureido)dodecanoic acid (AUDA)

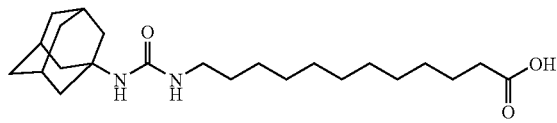 [SMILES: O=C(O)CCCCCCCCCCCNC(=O)NC12CC3CC(CC(C3)C1)C2]

12-(3-Adamantan-1-yl-ureido)dodecanoic acid butyl ester (AUDA-BE)

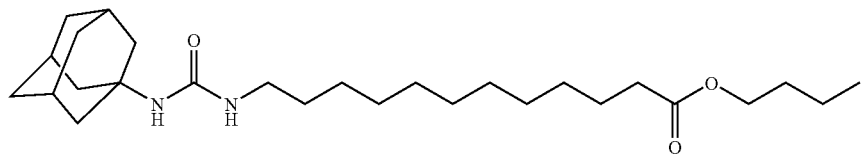 [SMILES: CCCCOC(=O)CCCCCCCCCCCNC(=O)NC12CC3CC(CC(C3)C1)C2]

Adamantan-1-yl-3-{5-[2-(2-ethoxyethoxy)ethoxy]pentyl}urea (compound 950)

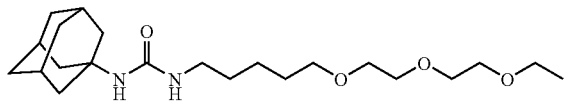 [SMILES: CCOCCOCCOCCCCCNC(=O)NC12CC3CC(CC(C3)C1)C2]

A number of other inhibitors, each of which is preferred for use in the methods and compositions of the invention, are set forth in co-owned applications PCT/US2004/010298 and U.S. Published Patent Application Publication 2005/0026844.

U.S. Pat. No. 5,955,496 (the '496 patent) sets forth a number of suitable epoxide hydrolase inhibitors for use in the methods of the invention. One category of inhibitors comprises inhibitors that mimic the substrate for the enzyme. The lipid alkoxides (e.g., the 9-methoxide of stearic acid) are an exemplar of this group of inhibitors. In addition to the inhibitors discussed in the '496 patent, a dozen or more lipid alkoxides have been tested as sEH inhibitors, including the methyl, ethyl, and propyl alkoxides of oleic acid (also known as stearic acid alkoxides), linoleic acid, and arachidonic acid, and all have been found to act as inhibitors of sEH.

In another group of embodiments, the '496 patent sets forth sEH inhibitors that provide alternate substrates for the enzyme that are turned over slowly. Exemplars of this category of inhibitors are phenyl glycidols (e.g., S,S-4-nitrophenylglycidol), and chalcone oxides. The '496 patent notes that suitable chalcone oxides include 4-phenylchalcone oxide and 4-fluourochalcone oxide. The phenyl glycidols and chalcone oxides are believed to form stable acyl enzymes.

Additional inhibitors of sEH suitable for use in the methods of the invention are set forth in U.S. Pat. No. 6,150,415 (the '415 patent) and U.S. Pat. No. 6,531,506 (the '506 patent). Two preferred classes of inhibitors of the invention are compounds of Formulas 1 and 2, as described in the '415 and '506 patents. Means for preparing such compounds and assaying desired compounds for the ability to inhibit epoxide hydrolases are also described. The '506 patent, in particular, teaches scores of inhibitors of Formula 1 and some twenty inhibitors of Formula 2, which were shown to inhibit human sEH at concentrations as low as 0.1 µM. Any particular inhibitor can readily be tested to determine whether it will work in the methods of the invention by standard assays, such as that set forth in the Examples, below. Esters and salts of the various compounds discussed above or in the cited patents, for example, can be readily tested by these assays for their use in the methods of the invention.

As noted above, chalcone oxides can serve as an alternate substrate for the enzyme. While chalcone oxides have half lives which depend in part on the particular structure, as a group the chalcone oxides tend to have relatively short half lives (a drug's half life is usually defined as the time for the concentration of the drug to drop to half its original value. See, e.g., Thomas, G., Medicinal Chemistry: an introduction, John Wiley & Sons Ltd. (West Sussex, England, 2000)). Since the uses of the invention contemplate inhibition of sEH over periods of time which can be measured in days, weeks, or months, chalcone oxides, and other inhibitors which have a half life whose duration is shorter than the practitioner deems desirable, are preferably administered in a manner which provides the agent over a period of time. For example, the inhibitor can be provided in materials that release the inhibitor slowly, including materials that release the inhibitor in or near the kidney, to provide a high local concentration. Methods of administration that permit high local concentrations of an inhibitor over a period of time are known, and are not limited to use with inhibitors which have short half lives although, for inhibitors with a relatively short half life, they are a preferred method of administration.

In addition to the compounds in Formula 1 of the '506 patent, which interact with the enzyme in a reversible fashion based on the inhibitor mimicking an enzyme-substrate transition state or reaction intermediate, one can have compounds that are irreversible inhibitors of the enzyme. The active structures such as those in the Tables or Formula 1 of the '506 patent can direct the inhibitor to the enzyme where a reactive functionality in the enzyme catalytic site can form a covalent bond with the inhibitor. One group of molecules, which could interact like this would have a leaving group such as a halogen or tosylate which could be attacked in an SN2 maimer with a lysine or histidine. Alternatively, the reactive functionality could be an epoxide or Michael acceptor such as an α/β-unsaturated ester, aldehyde, ketone, ester, or nitrile.

Further, in addition to the Formula 1 compounds, active derivatives can be designed for practicing the invention. For example, dicyclohexyl thio urea can be oxidized to dicyclohexylcarbodiimide which, with enzyme or aqueous acid (physiological saline), will form an active dicyclohexylurea. Alternatively, the acidic protons on carbamates or ureas can be replaced with a variety of substituents which, upon oxidation, hydrolysis or attack by a nucleophile such as glutathione, will yield the corresponding parent structure. These materials are known as prodrugs or protoxins (Gilman et al., The Pharmacological Basis of Therapeutics, 7th Edition, MacMillan Publishing Company, New York, p. 16 (1985)) Esters, for example, are common prodrugs which are released to give the corresponding alcohols and acids enzymatically (Yoshigae et al., Chirality, 9:661-666 (1997)). The drugs and prodrugs can be chiral for greater specificity. These derivatives have been extensively used in medicinal and agricultural chemistry to alter the pharmacological properties of the compounds such as enhancing water solubility, improving formulation chemistry, altering tissue targeting, altering volume of distribution, and altering penetration. They also have been used to alter toxicology profiles.

There are many prodrugs possible, but replacement of one or both of the two active hydrogens in the ureas described here or the single active hydrogen present in carbamates is particularly attractive. Such derivatives have been extensively described by Fukuto and associates. These derivatives have been extensively described and are commonly used in agricultural and medicinal chemistry to alter the pharmacological properties of the compounds. (Black et al., Journal of Agricultural and Food Chemistry, 21(5):747-751 (1973); Fahmy et al, Journal of Agricultural and Food Chemistry, 26(3):550-556 (1978); Jojima et al., Journal of Agricultural and Food Chemistry, 31(3):613-620 (1983); and Fahmy et al., Journal of Agricultural and Food Chemistry, 29(3):567-572 (1981).)

Such active proinhibitor derivatives are within the scope of the present invention, and the just-cited references are incorporated herein by reference. Without being bound by theory, it is believed that suitable inhibitors of the invention mimic the enzyme transition state so that there is a stable interaction with the enzyme catalytic site. The inhibitors appear to form hydrogen bonds with the nucleophilic carboxylic acid and a polarizing tyrosine of the catalytic site.

In some embodiments, sEH inhibition can include the reduction of the amount of sEH. As used herein, therefore, sEH inhibitors can therefore encompass nucleic acids that inhibit expression of a gene encoding sEH. Many methods of reducing the expression of genes, such as reduction of transcription and siRNA, are known, and are discussed in more detail below.

Preferably, the inhibitor inhibits sEH without also significantly inhibiting microsomal epoxide hydrolase ("mEH"). Preferably, at concentrations of 500 µM, the inhibitor inhibits sEH activity by at least 50% while not inhibiting mEH activity by more than 10%. Preferred compounds have an $IC_{50}$ (inhibition potency or, by definition, the concentration of inhibitor which reduces enzyme activity by 50%) of less than about 500 µM. Inhibitors with $IC_{50}$s of less than 500 µM are preferred, with $IC_{50}$s of less than 200 µM being more preferred, 100 µM being still more preferred and $IC_{50}$s of 50 µM, 40 µM, 30 µM, 25 µM, 20 µM, 15 µM, 10 µM, 5 µM, 3 µM, 2 µM, 1 µM or even less being the more preferred as the $IC_{50}$ decreases. Assays for determining sEH activity are known in the art and described elsewhere herein.

EETs

EETs, which are epoxides of arachidonic acid, are known to be effectors of blood pressure, regulators of inflammation, and modulators of vascular permeability. Hydrolysis of the epoxides by sEH diminishes this activity. Inhibition of sEH raises the level of EETs since the rate at which the EETs are hydrolyzed into dihydroxyeicosatrienoic acids ("DHETs") is reduced.

In the only prior report of topical administration of EETs of which we are aware, 11,12-EET was asserted to be useful in inhibiting the differentiation of fibroblasts to adipocytes. See U.S. Patent Application Publication 2004/0204487. In the methods of the present invention, however, 11,12-EET was found to be ineffective or less effective than other EETs. Accordingly, 11,12-EET is less preferred and preferably omitted in the compositions and methods of the invention.

EETs useful in the methods of the present invention include 14,15-EET, 8,9-EET and 5,6 EETs. Preferably, the EETs are administered as the methyl ester, which is more stable. Persons of skill will recognize that the EETs are regioisomers, such as 8S,9R- and 14R,15S-EET. 8,9-EET and 14R, 15S-EET, are commercially available from, for example, Sigma-Aldrich (catalog nos. E5516, E5641, and E5766, respectively, Sigma-Aldrich Corp., St. Louis, Mo.). 5,6-EET, 8,9-EET, and 14,15-EET are commercially available from, for example, Cayman Chemical Co. (Ann Arbor, Mich.).

If desired, EETs, analogs, or derivatives that retain activity can be used in place of or in combination with unmodified EETs. Liao and Zeldin, supra, define EET analogs as compounds with structural substitutions or alterations in an EET, and include structural analogs in which one or more EET olefins are removed or replaced with acetylene or cyclopropane groups, analogs in which the epoxide moiety is replaced with oxitane or furan rings and heteroatom analogs. In other analogs, the epoxide moiety is replaced with ether, alkoxides, difluorocyclopropane, or carbonyl, while in others, the carboxylic acid moiety is replaced with a commonly used mimic, such as a nitrogen heterocycle, a sulfonamide, or another polar functionality. In preferred forms, the analogs or derivatives are relatively stable as compared to an unmodified EET because they are more resistant than an EET to sEH and to chemical breakdown. "Relatively stable" means the rate of hydrolysis by sEH is at least 25% less than the hydrolysis of the unmodified EET in a hydrolysis assay, more preferably 50% or more lower than the rate of hydrolysis of an unmodified EET. Liao and Zeldin show, for example, episulfide and sulfonamide EETs derivatives. Amide and ester derivatives of EETs and that are relatively stable are preferred embodiments. In preferred forms, the analogs or derivatives have the biological activity of the unmodified EET regioisomer from which it is modified or derived in reducing pain or itching when applied topically. Whether or not a particular EET analog or derivative has the biological activity of the unmodified EET can be readily determined by using it in the assays described in the Examples. As mentioned in the Definition section, above, for convenience of reference, the term "EETs" as used herein refers to unmodified EETs, and EETs analogs and derivatives unless otherwise required by context.

In some embodiments, the EET or EETs are embedded or otherwise placed in a material that releases the EET over time. Materials suitable for promoting the slow release of compositions such as EETs are known in the art. Optionally, one or more sEH inhibitors may also be placed in the slow release material.

Conveniently, the EET or EETs can be administered orally. Since EETs are subject to degradation under acidic conditions, EETs intended for oral administration can be coated with a coating resistant to dissolving under acidic conditions, but which dissolve under the mildly basic conditions present in the intestines. Suitable coatings, commonly known as "enteric coatings" are widely used for products, such as aspirin, which cause gastric distress or which would undergo degradation upon exposure to gastric acid. By using coatings with an appropriate dissolution profile, the coated substance can be released in a chosen section of the intestinal tract. For example, a substance to be released in the colon is coated with a substance that dissolves at pH 6.5-7, while substances to be released in the duodenum can be coated with a coating that dissolves at pH values over 5.5. Such coatings are commercially available from, for example, Rohm Specialty Acrylics (Rohm America LLC, Piscataway, N.J.) under the trade name "Eudragit®". The choice of the particular enteric coating is not critical to the practice of the invention.

Assays for Epoxide Hydrolase Activity

Any of a number of standard assays for determining epoxide hydrolase activity can be used to determine inhibition of sEH. For example, suitable assays are described in Gill, et al., Anal Biochem 131, 273-282 (1983); and Borhan, et al., Analytical Biochemistry 231, 188-200 (1995)). Suitable in vitro assays are described in Zeldin et al., J Biol. Chem. 268:6402-6407 (1993). Suitable in vivo assays are described in Zeldin et al., Arch Biochem Biophys 330:87-96 (1996). Assays for epoxide hydrolase using both putative natural substrates and surrogate substrates have been reviewed (see, Hammock, et al. In: Methods in Enzymology, Volume III, Steroids and Isoprenoids, Part B, (Law, J. H. and H. C. Rilling, eds. 1985), Academic Press, Orlando, Fla., pp. 303-311 and Wixtrom et al., In: Biochemical Pharmacology and Toxicology, Vol. 1: Methodological Aspects of Drug Metabolizing Enzymes, (Zakim, D. and D. A. Vessey, eds. 1985), John Wiley & Sons, Inc., New York, pp. 1-93. Several spectral based assays exist based on the reactivity or tendency of the resulting diol product to hydrogen bond (see, e.g., Wixtrom, supra, and Hammock. Anal. Biochem. 174:291-299 (1985) and Dietze, et al. Anal. Biochem. 216:176-187 (1994)).

The enzyme also can be detected based on the binding of specific ligands to the catalytic site which either immobilize the enzyme or label it with a probe such as dansyl, fluoracein, luciferase, green fluorescent protein or other reagent. The enzyme can be assayed by its hydration of EETs, its hydrolysis of an epoxide to give a colored product as described by Dietze et al., 1994, supra, or its hydrolysis of a radioactive surrogate substrate (Borhan et al., 1995, supra). The enzyme also can be detected based on the generation of fluorescent products following the hydrolysis of the epoxide. Numerous method of epoxide hydrolase detection have been described (see, e.g., Wixtrom, supra).

The assays are normally carried out with a recombinant enzyme following affinity purification. They can be carried out in crude tissue homogenates, cell culture or even in vivo, as known in the art and described in the references cited above.

Other Means of Inhibiting sEH Activity

Other means of inhibiting sEH activity or gene expression can also be used in the methods of the invention. For example, a nucleic acid molecule complementary to at least a portion of the human sEH gene can be used to inhibit sEH gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through a mRNA degradation pathway, while stRNAs and miRNAs are approximately 21 or 22 nt RNAs that are processed from endogenously encoded hairpin-structured precursors, and function to silence genes via translational repression. See, e.g., McManus et al., RNA, 8(6):842-50 (2002); Morris et al., Science. 305(5688):1289-92 (2004); He and Hannon, Nat Rev Genet. 5(7):522-31 (2004).

"RNA interference," a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo. In mammalian cells other than these, however, longer RNA duplexes provoked a response known as "sequence non-specific RNA interference," characterized by the non-specific inhibition of protein synthesis.

Further studies showed this effect to be induced by dsRNA of greater than about 30 base pairs, apparently due to an interferon response. It is thought that dsRNA of greater than about 30 base pairs binds and activates the protein PKR and 2',5'-oligonucleotide synthetase (2',5'-AS). Activated PKR stalls translation by phosphorylation of the translation initiation factors eIF2α, and activated 2',5'-AS causes mRNA degradation by 2',5'-oligonucleotide-activated ribonuclease L. These responses are intrinsically sequence-nonspecific to the inducing dsRNA; they also frequently result in apoptosis, or cell death. Thus, most somatic mammalian cells undergo apoptosis when exposed to the concentrations of dsRNA that induce RNAi in lower eukaryotic cells.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of sEH, siRNAs to the gene encoding sEH can be specifically designed using computer programs. The cloning, sequence, and accession numbers of the human sEH sequence are set forth in Beetham et al., Arch. Biochem. Biophys. 305(1):197-201 (1993). The amino acid sequence of human sEH is also set forth as SEQ ID NO:2 of U.S. Pat. No. 5,445,956; nucleotides 42-1703 of SEQ ID NO:1 are the nucleic acid sequence encoding the amino acid sequence.

A program, siDESIGN from Dharmacon, Inc. (Lafayette, Colo.), permits predicting siRNAs for any nucleic acid sequence, and is available on the World Wide Web at dharmacon.com. Programs for designing siRNAs are also available from others, including Genscript (available on the Web at genscript.com/ssl-bin/app/rnai) and, to academic and non-profit researchers, from the Whitehead Institute for Biomedical Research on the internet by entering "http://" followed by "jura.wi.mit.edu/pubint/http://iona.wi.mit.edu/siRNAext/."

For example, using the program available from the Whitehead Institute, the following sEH target sequences and siRNA sequences can be generated:

1) Target:
CAGTGTTCATTGGCCATGACTGG             (SEQ ID NO: 3)

-continued

```
Sense-siRNA:
5'- GUGUUCAUUGGCCAUGACUTT- 3'      (SEQ ID NO: 4)

Antisense-siRNA:
5'- AGUCAUGGCCAAUGAACACTT- 3'      (SEQ ID NO: 5)

2) Target:
GAAAGGCTATGGAGAGTCATCTG            (SEQ ID NO: 6)

Sense-siRNA:
5'- AAGGCUAUGGAGAGUCAUCTT- 3'      (SEQ ID NO: 7)

Antisense-siRNA:
5'- GAUGACUCUCCAUAGCCUUTT- 3'      (SEQ ID NO: 8)

3) Target
AAAGGCTATGGAGAGTCATCTGC            (SEQ ID NO: 9)

Sense-siRNA:
5'- AGGCUAUGGAGAGUCAUCUTT- 3'      (SEQ ID NO: 10)

Antisense-siRNA:
5'- AGAUGACUCUCCAUAGCCUTT- 3'      (SEQ ID NO: 11)

4) Target:
CAAGCAGTGTTCATTGGCCATGA            (SEQ ID NO: 12)

Sense-siRNA:
5'- AGCAGUGUUCAUUGGCCAUTT- 3'      (SEQ ID NO: 13)

Antisense-siRNA:
5'- AUGGCCAAUGAACACUGCUTT- 3'      (SEQ ID NO: 14)

5) Target:
CAGCACATGGAGGACTGGATTCC            (SEQ ID NO: 15)

Sense-siRNA:
5'- GCACAUGGAGGACUGGAUUTT- 3'      (SEQ ID NO: 16)

Antisense-siRNA:
5'- AAUCCAGUCCUCCAUGUGCTT- 3'      (SEQ ID NO: 17)
```

Alternatively, siRNA can be generated using kits which generate siRNA from the gene. For example, the "Dicer siRNA Generation" kit (catalog number T510001, Gene Therapy Systems, Inc., San Diego, Calif.) uses the recombinant human enzyme "dicer" in vitro to cleave long double stranded RNA into 22 bp siRNAs. By having a mixture of siRNAs, the kit permits a high degree of success in generating siRNAs that will reduce expression of the target gene. Similarly, the Silencer™ siRNA Cocktail Kit (RNase III) (catalog no. 1625, Ambion, Inc., Austin, Tex.) generates a mixture of siRNAs from dsRNA using RNase III instead of dicer. Like dicer, RNase III cleaves dsRNA into 12-30 bp dsRNA fragments with 2 to 3 nucleotide 3' overhangs, and 5'-phosphate and 3'-hydroxyl termini. According to the manufacturer, dsRNA is produced using T7 RNA polymerase, and reaction and purification components included in the kit. The dsRNA is then digested by RNase III to create a population of siRNAs. The kit includes reagents to synthesize long dsRNAs by in vitro transcription and to digest those dsRNAs into siRNA-like molecules using RNase III. The manufacturer indicates that the user need only supply a DNA template with opposing T7 phage polymerase promoters or two separate templates with promoters on opposite ends of the region to be transcribed.

The siRNAs can also be expressed from vectors. Typically, such vectors are administered in conjunction with a second vector encoding the corresponding complementary strand. Once expressed, the two strands anneal to each other and form the functional double stranded siRNA. One exemplar vector suitable for use in the invention is pSuper, available from OligoEngine, Inc. (Seattle, Wash.). In some embodiments, the vector contains two promoters, one positioned downstream of the first and in antiparallel orientation. The first promoter is transcribed in one direction, and the second in the direction antiparallel to the first, resulting in expression of the complementary strands. In yet another set of embodiments, the promoter is followed by a first segment encoding the first strand, and a second segment encoding the second strand. The second strand is complementary to the palindrome of the first strand. Between the first and the second strands is a section of RNA serving as a linker (sometimes called a "spacer") to permit the second strand to bend around and anneal to the first strand, in a configuration known as a "hairpin."

The formation of hairpin RNAs, including use of linker sections, is well known in the art. Typically, an siRNA expression cassette is employed, using a Polymerase III promoter such as human U6, mouse U6, or human H1. The coding sequence is typically a 19-nucleotide sense siRNA sequence linked to its reverse complementary antisense siRNA sequence by a short spacer. Nine-nucleotide spacers are typical, although other spacers can be designed. For example, the Ambion website indicates that its scientists have had success with the spacer TTCAAGAGA (SEQ ID NO:18). Further, 5-6 T's are often added to the 3' end of the oligonucleotide to serve as a termination site for Polymerase III. See also, Yu et al., Mol Ther 7(2):228-36 (2003); Matsukura et al., Nucleic Acids Res 31(15):e77 (2003).

As an example, the siRNA targets identified above can be targeted by hairpin siRNA as follows. To attack the same targets by short hairpin RNAs, produced by a vector (permanent RNAi effect), sense and antisense strand can be put in a row with a loop forming sequence in between and suitable sequences for an adequate expression vector to both ends of the sequence. The following are non-limiting examples of hairpin sequences that can be cloned into the pSuper vector:

```
1) Target:
CAGTGTTCATTGGCCATGACTGG            (SEQ ID NO: 19)

Sense strand:
5'-GATCCCCGTGTTCATTGGCCATGACTTTCAA (SEQ ID NO: 20)

GAGAAGTCATGGCCAATGAACACTTTTT-3'

Antisense strand:
5'-AGCTAAAAAGTGTTCATTGGCCATGACTTCT (SEQ ID NO: 21)

CTTGAAAGTCATGGCCAATGAACACGGG-3'

2) Target:
GAAAGGCTATGGAGAGTCATCTG            (SEQ ID NO: 22)

Sense strand:
5'-GATCCCCAAGGCTATGGAGAGTCATCTTCAA (SEQ ID NO: 23)

GAGAGATGACTCTCCATAGCCTTTTTT-3'

Antisense strand:
5'-AGCTAAAAAAGGCTATGGAGAGTCATCTCT  (SEQ ID NO: 24)

CTTGAAGATGACTCTCCATAGCCTTGGG-3'

3) Target:
AAAGGCTATGGAGAGTCATCTGC            (SEQ ID NO: 25)

Sense strand:
5'-GATCCCCAGGCTATGGAGAGTCATCTTTCAA (SEQ ID NO: 26)

GAGAAGATGACTCTCCATAGCCTTTTTT-3'
```

```
Antisense strand:
5'-                                    (SEQ ID NO: 27)
AGCTAAAAAAGGCTATGGAGAGTCATCATCTCTT
GAAAGATGACTCTCCATAGCCTGGG-3'

4) Target:
CAAGCAGTGTTCATTGGCCATGA                (SEQ ID NO: 28)

Sense strand:
5'-GATCCCCAGCAGTGTTCATTGGCCATTTCAA     (SEQ ID NO: 29)
GAGAATGGCCAATGAACACTGCTTTTTT-3'

Antisense strand:
5'-AGCTAAAAAGCAGTGTTCATTGGCCATTCT      (SEQ ID NO: 30)
CTTGAAATGGCCAATGAACACTGCTGGG-3'

5) Target:
CAGCACATGGAGGACTGGATTCC                (SEQ ID NO: 31)

Sense strand
5'-GATCCCCGCACATGGAGGACTGGATTTTCAA     (SEQ ID NO: 32)
GAGAAATCCAGTCCTCCATGTGCTTTTT-3'

Antisense strand:
5'-AGCTAAAAAGCACATGGAGGACTGGATTTCT     (SEQ ID NO: 33)
CTTGAAAATCCAGTCCTCCATGTGCGGG-3'
```

In addition to siRNAs, other means are known in the art for inhibiting the expression of antisense molecules, ribozymes, and the like are well known to those of skill in the art. The nucleic acid molecule can be a DNA probe, a riboprobe, a peptide nucleic acid probe, a phosphorothioate probe, or a 2'-O methyl probe.

Generally, to assure specific hybridization, the antisense sequence is substantially complementary to the target sequence. In certain embodiments, the antisense sequence is exactly complementary to the target sequence. The antisense polynucleotides may also include, however, nucleotide substitutions, additions, deletions, transitions, transpositions, or modifications, or other nucleic acid sequences or non-nucleic acid moieties so long as specific binding to the relevant target sequence corresponding to the sEH gene is retained as a functional property of the polynucleotide. In one embodiment, the antisense molecules form a triple helix-containing, or "triplex" nucleic acid. Triple helix formation results in inhibition of gene expression by, for example, preventing transcription of the target gene (see, e.g., Cheng et al., 1988, J. Biol. Chem. 263:15110; Ferrin and Camerini-Otero, 1991, Science 354:1494; Ramdas et al., 1989, J. Biol. Chem. 264: 17395; Strobel et al., 1991, Science 254:1639; and Rigas et al., 1986, Proc. Natl. Acad. Sci. U.S.A. 83:9591)

Antisense molecules can be designed by methods known in the art. For example, Integrated DNA Technologies (Coralville, Iowa) makes available a program on the internet which can be found by entering http://, followed by biotools.idtdna.com/antisense/AntiSense.aspx, which will provide appropriate antisense sequences for nucleic acid sequences up to 10,000 nucleotides in length. Using this program with the sEH gene provides the following exemplar sequences:

```
1)   UGUCCAGUGCCCACAGUCCU        (SEQ ID NO: 34)
2)   UUCCCACCUGACACGACUCU        (SEQ ID NO: 35)
3)   GUUCAGCCUCAGCCACUCCU        (SEQ ID NO: 36)
4)   AGUCCUCCCGCUUCACAGA         (SEQ ID NO: 37)
5)   GCCCACUUCCAGUUCCUUUCC       (SEQ ID NO: 38)
```

In another embodiment, ribozymes can be designed to cleave the mRNA at a desired position. (See, e.g., Cech, 1995, Biotechnology 13:323; and Edgington, 1992, Biotechnology 10:256 and Hu et al., PCT Publication WO 94/03596).

The antisense nucleic acids (DNA, RNA, modified, analogues, and the like) can be made using any suitable method for producing a nucleic acid, such as the chemical synthesis and recombinant methods disclosed herein and known to one of skill in the art. In one embodiment, for example, antisense RNA molecules of the invention may be prepared by de novo chemical synthesis or by cloning. For example, an antisense RNA can be made by inserting (ligating) a sEH gene sequence in reverse orientation operably linked to a promoter in a vector (e.g., plasmid). Provided that the promoter and, preferably termination and polyadenylation signals, are properly positioned, the strand of the inserted sequence corresponding to the noncoding strand will be transcribed and act as an antisense oligonucleotide of the invention.

It will be appreciated that the oligonucleotides can be made using nonstandard bases (e.g., other than adenine, cytidine, guanine, thymine, and uridine) or nonstandard backbone structures to provides desirable properties (e.g., increased nuclease-resistance, tighter-binding, stability or a desired Tm). Techniques for rendering oligonucleotides nuclease-resistant include those described in PCT Publication WO 94/12633. A wide variety of useful modified oligonucleotides may be produced, including oligonucleotides having a peptide-nucleic acid (PNA) backbone (Nielsen et al., 1991, Science 254:1497) or incorporating 2'-O-methyl ribonucleotides, phosphorothioate nucleotides, methyl phosphonate nucleotides, phosphotriester nucleotides, phosphorothioate nucleotides, phosphoramidates.

Proteins have been described that have the ability to translocate desired nucleic acids across a cell membrane. Typically, such proteins have amphiphilic or hydrophobic subsequences that have the ability to act as membrane-translocating carriers. For example, homeodomain proteins have the ability to translocate across cell membranes. The shortest internalizable peptide of a homeodomain protein, Antennapedia, was found to be the third helix of the protein, from amino acid position 43 to 58 (see, e.g., Prochiantz, Current Opinion in Neurobiology 6:629-634 (1996). Another subsequence, the h (hydrophobic) domain of signal peptides, was found to have similar cell membrane translocation characteristics (see, e.g., Lin et al., J. Biol. Chem. 270:14255-14258 (1995)). Such subsequences can be used to translocate oligonucleotides across a cell membrane. Oligonucleotides can be conveniently derivatized with such sequences. For example, a linker can be used to link the oligonucleotides and the translocation sequence. Any suitable linker can be used, e.g., a peptide linker or any other suitable chemical linker.

More recently, it has been discovered that siRNAs can be introduced into mammals without eliciting an immune response by encapsulating them in nanoparticles of cyclodextrin. Information on this method can be found by entering "www." followed by "nature.com/news/2005/050418/full/050418-6.html."

In another method, the nucleic acid is introduced directly into superficial layers of the skin or into muscle cells by a jet of compressed gas or the like. Methods for administering naked polynucleotides are well known and are taught, for example, in U.S. Pat. No. 5,830,877 and International Publication Nos. WO 99/52483 and 94/21797. Devices for accelerating particles into body tissues using compressed gases are described in, for example, U.S. Pat. Nos. 6,592,545, 6,475,181, and 6,328,714. The nucleic acid may be lyophilized and may be complexed, for example, with polysaccharides to form a particle of appropriate size and mass for acceleration into tissue. Conveniently, the nucleic acid can be placed on a gold bead or other particle which provides suitable mass or other characteristics. Use of gold beads to carry nucleic acids into body tissues is taught in, for example, U.S. Pat. Nos. 4,945,050 and 6,194,389.

The nucleic acid can also be introduced into the body in a virus modified to serve as a vehicle without causing pathogenicity. The virus can be, for example, adenovirus, fowlpox virus or vaccinia virus.

miRNAs and siRNAs differ in several ways: miRNA derive from points in the genome different from previously recognized genes, while siRNAs derive from mRNA, viruses or transposons, miRNA derives from hairpin structures, while siRNA derives from longer duplexed RNA, miRNA is conserved among related organisms, while siRNA usually is not, and miRNA silences loci other than that from which it derives, while siRNA silences the loci from which it arises. Interestingly, miRNAs tend not to exhibit perfect complementarity to the mRNA whose expression they inhibit. See, McManus et al., supra. See also, Cheng et al., Nucleic Acids Res. 33(4): 1290-7 (2005); Robins and Padgett, Proc Natl Acad Sci USA. 102(11):4006-9 (2005); Brennecke et al., PLoS Biol. 3(3):e85 (2005). Methods of designing miRNAs are known. See, e.g., Zeng et al., Methods Enzymol. 392:371-80 (2005); Krol et al., J Biol Chem. 279(40):42230-9 (2004); Ying and Lin, Biochem Biophys Res Commun. 326(3):515-20 (2005).

Therapeutic Administration

A variety of solid, semisolid and liquid vehicles have been known in the art for years for for topical application of agents to the skin. Such vehicles include creams, lotions, gels, balms, oils, ointments and sprays. See, e.g., Provost C. "Transparent oil-water gels: a review," Int J Cosmet Sci. 8:233-247 (1986), Katz and Poulsen, Concepts in biochemical pharmacology, part I. In: Brodie B B, Gilette J R, eds. Handbook of Experimental Pharmacology. Vol. 28. New York, N.Y.: Springer; 107-174 (1971), and Hadgcraft, "Recent progress in the formulation of vehicles for topical applications," Br J Dermatol., 81:386-389 (1972). A number of topical formulations of analgesics, including capsaicin (e.g., Capsin®), so-called "counter-irritants" (e.g., Icy-Hot®), substances such as menthol, oil of wintergreen, camphor, or eucalyptus oil compounds which, when applied to skin over an area presumably alter or off-set pain in joints or muscles served by the same nerves) and salicylates (e.g. BenGay®), are known and can be readily adapted for topical administration of sEHI by replacing the active ingredient or ingredient with an sEHI, with or without EETs. It is presumed that the person of skill is familiar with these various vehicles and preparations and they need not be described in detail herein.

Inhibitors of sEHI, or EETs, or both, (the "agents") can be mixed into such modalities (creams, lotions, gels, etc.) for topical administration. In general, the concentration of the agents provides a gradient which drives the agent into the skin. Standard ways of determining flux of drugs into the skin, as well as for modifying agents to speed or slow their delivery into the skin are well known in the art and taught, for example, in Osborne and Amann, eds., Topical Drug Delivery Formulations, Marcel Dekker, 1989. The use of dermal drug delivery agents in particular is taught in, for example, Ghosh et al., eds., Transdermal and Topical Drug Delivery Systems, CRC Press, (Boca Raton, Fla., 1997).

In some embodiments, the agents are in a cream. Typically, the cream comprises one or more hydrophobic lipids, with other agents to improve the "feel" of the cream or to provide other useful characteristics. In one embodiment, for example, a cream of the invention may contain 0.01 mg to 10 mg of sEHI, with or without one or more EETs, per gram of cream in a white to off-white, opaque cream base of purified water USP, white petrolatum USP, stearyl alcohol NF, propylene glycol USP, polysorbate 60 NF, cetyl alcohol NF, and benzoic acid USP 0.2% as a preservative. In the studies reported in the Examples, sEHI were mixed into a commercially available cream, Vanicream® (Pharmaceutical Specialties, Inc., Rochester, Minn.) comprising purified water, white petrolatum, cetearyl alcohol and ceteareth-20, sorbitol solution, propylene glycol, simethicone, glyceryl monostearate, polyethylene glycol monostearate, sorbic acid and BHT.

In other embodiments, the agent or agents are in a lotion. Typical lotions comprise, for example, water, mineral oil, petrolatum, sorbitol solution, stearic acid, lanolin, lanolin alcohol, cetyl alcohol, glyceryl stearate/PEG-100 stearate, triethanolamine, dimethicone, propylene glycol, microcrystalline wax, tri (PPG-3 myristyl ether) citrate, disodium EDTA, methylparaben, ethylparaben, propylparaben, xanthan gum, butylparaben, and methyldibromo glutaronitrile.

In some embodiments, the agent is, or agents are, in an oil, such as jojoba oil. In some embodiments, the agent is, or agents are, in an ointment, which may, for example, white petrolatum, hydrophilic petrolatum, anhydrous lanolin, hydrous lanolin, or polyethylene glycol. In some embodiments, the agent is, or agents are, in a spray, which typically comprise an alcohol and a propellant. If absorption through the skin needs to be enhanced, the spray may optionally contain, for example, isopropyl myristate.

Whatever the form in which the agents are administered (that is, whether by lotion, gel, spray, etc.), they are preferably administered at a dosage of about 0.01 mg to 10 mg per 10 cm$^2$.

EETs, or sEHI, or both, can be introduced into the bowel by use of a suppository. As is known in the art, suppositories are solid compositions of various sizes and shapes intended for introduction into body cavities. Typically, the suppository comprises a medication, which is released into the immediate area from the suppository. Typically, suppositories are made using a fatty base, such as cocoa butter, that melts at body temperature, or a water-soluble or miscible base, such as glycerinated gelatin or polyethylene glycol.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. A therapeutically effective amount of the sEH inhibitor, or EETs, or both, is employed in relieving pain in the patient.

EXAMPLES

Example 1

The hyperalgesic response with the hind paw withdrawal test is considered to result from a combination of central and peripheral mechanisms (Kannan et al., "Endotoxin-induced local inflammation and hyperalgesia in rats mice, a new model for inflammatory pain," Pharmacology 66:373-379 (1996)). We used the method of Hargreaves et al., "A new and sensitive method for measuring thermal nociception in cutaneous hyperalgesia", Pain 32, 77-88 (1988) to quantify the pain response of rats treated with two sEH inhibitors and EETs.

Example 2

Pain was quantified using the hind paw withdrawal latency test. Male Sprague-Dawley rats (Charles River Laboratories, Inc., Wilmington, Mass.) weighing 250-300 g, were used. Animals were individually housed at UC Davis Animal Resource Facility under standard conditions with free access to food and water, and maintained for at least 1 week before the experiments. Each rat was used only once. All the experiments were performed during the daytime between 8.00 and 13.00 h (during the first phase of the light period of the diurnal cycle). Rats were first trained to the experimental chamber in three separate sessions. In the day of the experiments rats' basal response was measured and then they were treated with a neutral cream or compound containing formulated cream preceding an injection with 10 ug of endotoxin (Lipopolysaccharide, "LPS") or capsaicin in the right hind paw to induce pain response. Pain response was then measured at 30, 60, 120 and 240 minutes post LPS or capsaicin injection. sEHIs were formulated by dissolving them in ethanol and mixing with cream in a ratio of 1:9. Eight animals per group were used.

Example 3

Figure 4:
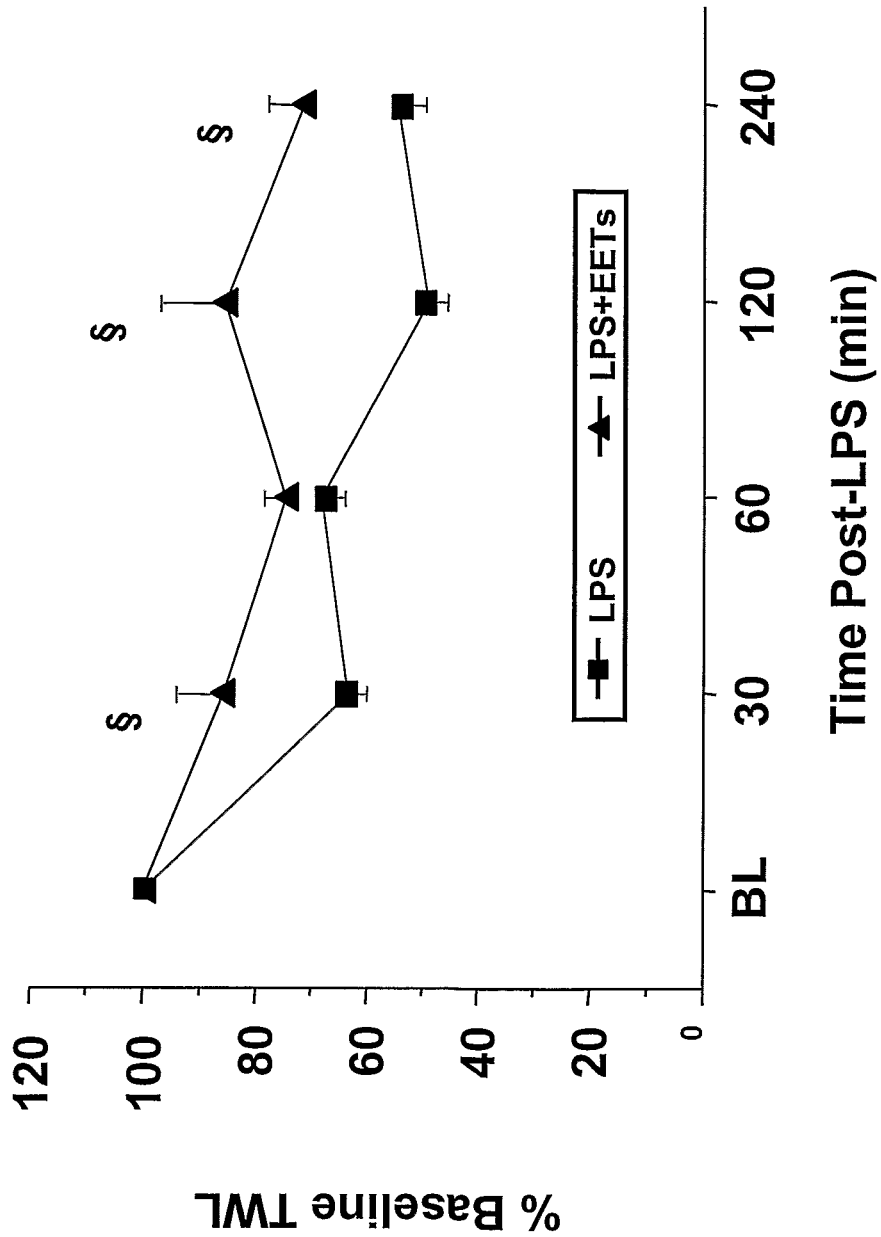
FIG. 4 shows that EETs block LPS-elicited mechanical allodynia thermal hyperalgesia. Filled squares are LPS (10 μg). Filled triangles: mixture of EETs at 50 mg/kg. Section symbols: shows statistically significant results.
Figure 5:
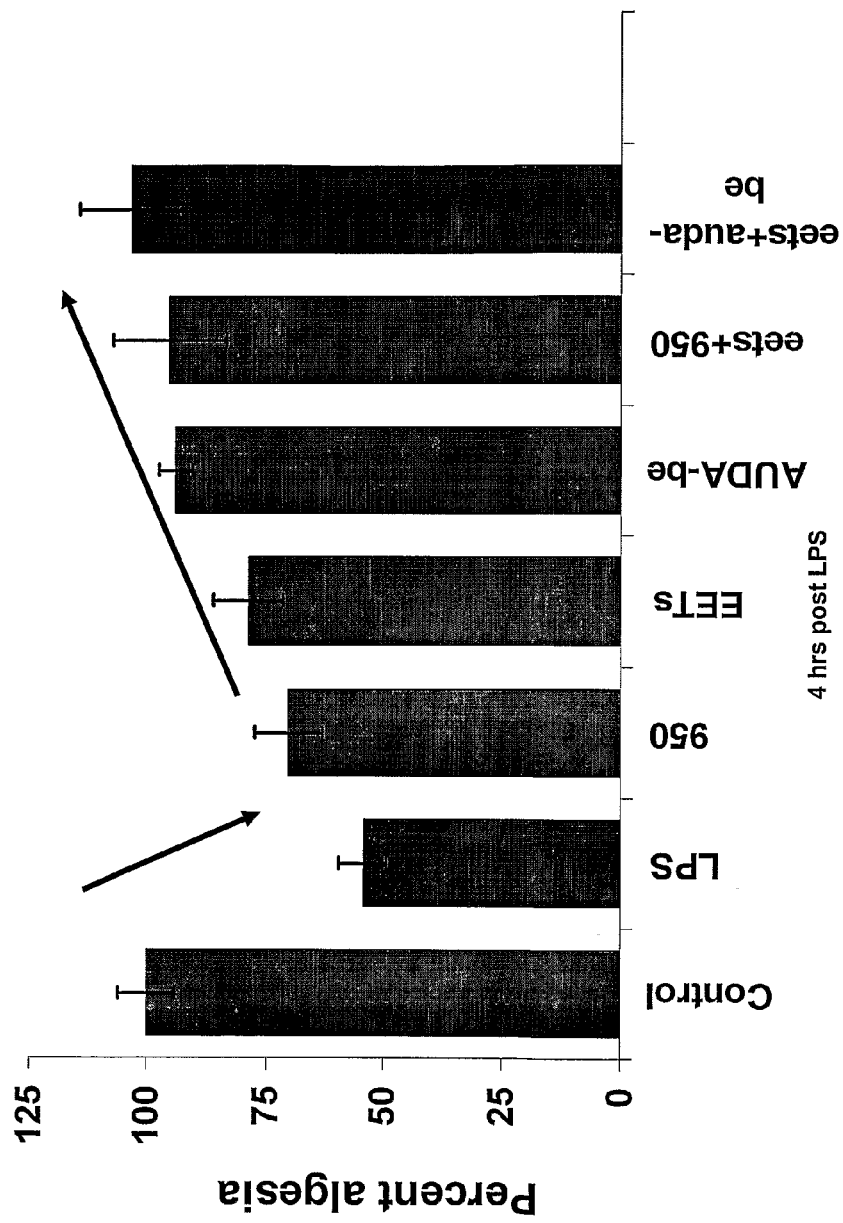
FIG. 5 is a graph comparing the analgesic effect of various sEH inhibitors, EETs and combinations thereof to untreated animals. Y axis shows the percent of analgesia induced by the various agents compared to the control (vehicle). X axis: shows the particular agent tested. Testing was conducted 4 hours after exposure to LPS.
Figure 6:
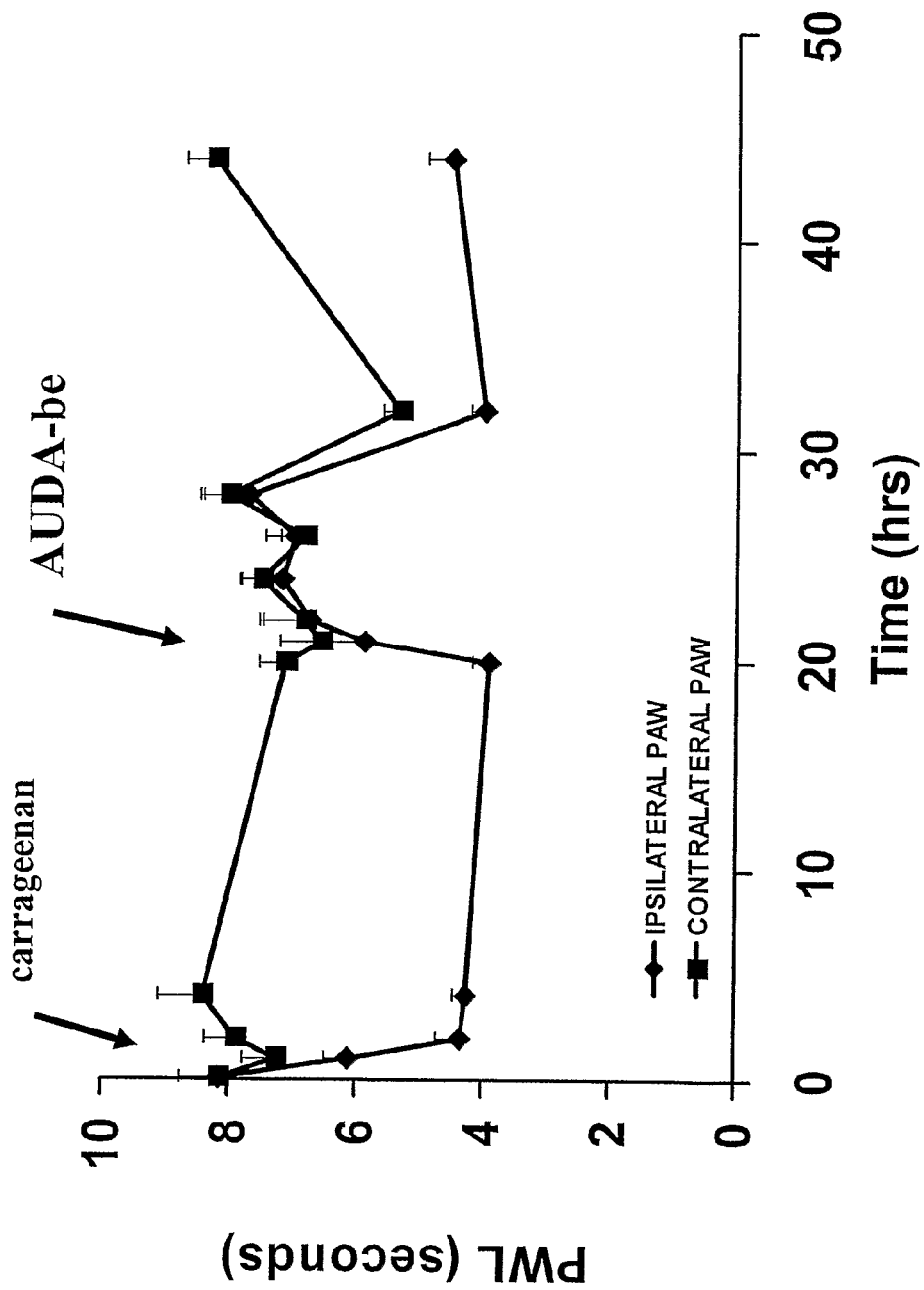
FIG. 6 is a graph showing that the sEH inhibitor AUDA-be blocks carrageenan-elicited thermal hyperalgesia. X axis shows time in hours. Y axis shows thermal withdrawal latency of the animal's paw (here listed as "PWL") in seconds. Animals were exposed to carrageenan at time 0 by injection into ipsilateral paw, the contralateral paw was left untreated. AUDA-be was administered at 20 hours post-exposure to the carrageenan. Filled diamonds are the withdrawal tests of the treated paw. Filled squares are the tests of the untreated paw.

To assess thermal nociceptive responses, a commercially available device modeled after that described by Hargreaves et al., supra, was employed. This device consists of a glass surface upon which the rats are placed individually in Plexiglass cubicles (9×22×25 cm). The glass surface temperature is maintained at either 30.1° C. by a feedback-controlled, under-glass, forced-air heating system. The heating system is driven by a thermocouple attached to the bottom surface of the glass plate. The thermal nociceptive stimulus originates from a focused projection bulb mounted in a stimulus tower that is manually manipulated in a two-dimensional axis to permit the stimulus to be delivered to hind paw of each test subject. A timer is automatically actuated with the light source, and response latency is defined as the time required for the paw to show an abrupt withdrawal. Paw withdrawal is detected by a photodiode motion sensor mounted on the stimulus tower that stops the timer and terminates the stimulus. In all cases, a cut-off of 20 seconds is employed to avoid tissue injury. See also, Dirig et al., "Characterization of variables defining hindpaw withdrawal latency evoked by radiant thermal stimuli," J Neuroscience Methods 76: 183-191 (1997). Results of tests using two different sEH inhibitors on LPS-elicited thermal hyperalgesia are shown in FIG. 1. EETs were also found to block LPS-elicited thermal hyperalgesia, as shown in FIG. 4. The sEH inhibitor AUDA-be was also shown to block carrageenan-elicited thermal hyperalgesia, as shown in FIG. 6. 1

Example 4

For the quantification of mechanical allodynia, a set of von Frey filaments with different diameters corresponding to different quantities of force applied were employed. The baseline responses of animals were first determined and than LPS was injected in the hind paw. Responses were measured 1 hr and 2 hrs after LPS injection. Eight animals per group were used. Rats' paws were stimulated with filaments of increasing diameter three times. The diameter of filaments that rats withdraw their paws were recorded.

When animals were treated only with cream and LPS, they showed a drastic reduction in their withdrawal latencies. This effect is more pronounced in later times such as 2 and 4 hours post injection. However the pain response is restored towards the baseline levels with the application of sEH inhibitors, EETs and with a combination of these two treatments. Interestingly the combination of sEH inhibitors and EETs is more effective then either treatment alone in reducing pain.

Figure 3:
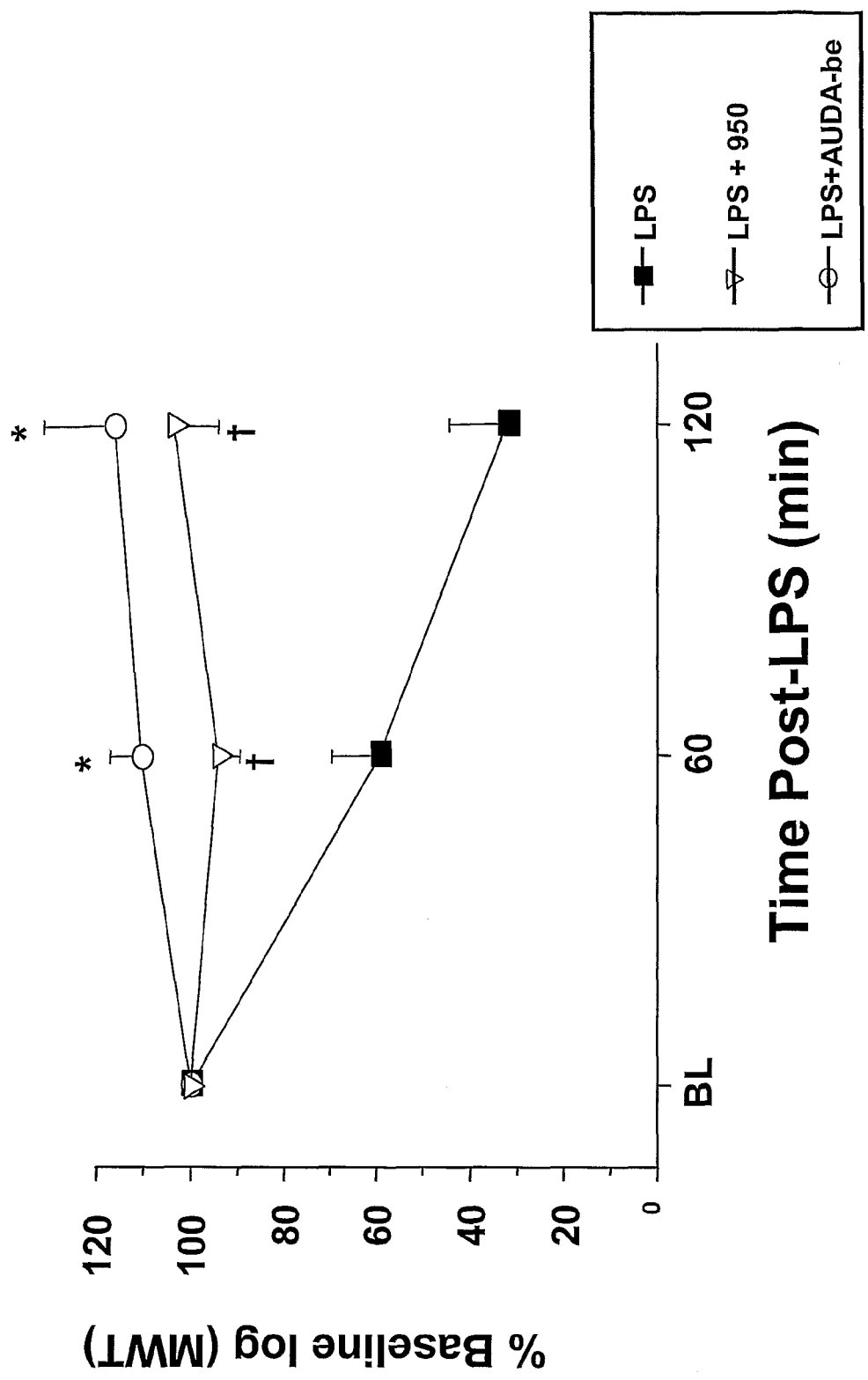
FIG. 3 shows that two sEH inhibitors block LPS-elicited mechanical allodynia. AUDA-be and 950 are two sEH inhibitors. X axis shows time post-LPS exposure. Y axis is percent mechanical withdrawal threshold ("MWT"). Circles: AUDA-be (50 mg/kg)+LPS (10 μg). Triangles: compound 950 (50 mg/kg)+LPS (10 μg). Filled squares are LPS (10 μg). Asterisks and crosses denote statistically significant results.

LPS injection significantly reduced the paw withdrawal response of the animals. In contrast animals treated with sEHIs not only did not show decline in their response but their ability to endure mechanical force was increased significantly over their baseline responses. FIG. 3 shows that two exemplar sEH inhibitors blocked LPS-elicited mechanical allodynia.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of relieving neuropathic pain in a subject, said method comprising topically administering to said subject an effective amount of an inhibitor of soluble epoxide hydrolase ("sEH"), thereby relieving neuropathic pain in said subject, wherein the inhibitor of sEH has a pharmacophore that is a urea, a carbamate or an amide.

2. A method of claim 1, wherein the pain relieved is from a burn.

3. A method of claim 1, wherein the pain is from post-herpetic neuralgia.

4. A method of claim 1, further comprising topically administering an epoxide of a polyunsaturated fatty acid.

5. A method of claim 4, wherein said epoxide is a cis-epoxyeicosatrienoic acid ("EET").

6. A method of claim 5, wherein said EET is selected from the group consisting of 5,6-EET, 14,15-EET, 8,9-EET, and 11,12-EET.

7. A method of claim 1, wherein said subject does not have hypertension, or is not being treated for hypertension with an inhibitor of sEH.

8. A method of claim 1, wherein said inhibitor of sEH is administered to an area of skin one hour or less before a dermatological procedure or cosmetic surgery on said area of skin to relieve pain associated with said procedure or surgery.

9. A method of claim 1, wherein said topical administration is by a suppository comprising said inhibitor of sEHI.

10. A method of claim 1, wherein said inhibitor of sEH inhibits sEH with an IC50 of less than about 500 μM.

11. A method of claim 1, wherein the pain relieved is pain in the extremities from diabetic neuropathy.

* * * * *

SEQUENCE LISTING

```
<160> NUMBER OF SEQ ID NOS: 38

<210> SEQ ID NO 1
<211> LENGTH: 554
<212> TYPE: PRT
<213> ORGANISM: Homo sapiens
<220> FEATURE:
<223> OTHER INFORMATION: human soluble epoxide hydrolase (sEH,
      cytosolic EH)

<400> SEQUENCE: 1

Met Thr Leu Arg Gly Ala Val Phe Asp Leu Asp Gly Val Leu Ala Leu
1               5                   10                  15

Pro Ala Val Phe Gly Val Leu Gly Arg Thr Glu Glu Ala Leu Ala Leu
            20                  25                  30
```

```
Pro Arg Gly Leu Leu Asn Asp Ala Phe Gln Lys Gly Pro Glu Gly
            35                  40                  45
Ala Thr Thr Arg Leu Met Lys Gly Glu Ile Thr Leu Ser Gln Trp Ile
 50                      55                  60
Pro Leu Met Glu Glu Asn Cys Arg Lys Cys Ser Glu Thr Ala Lys Val
 65                  70                  75                  80
Cys Leu Pro Lys Asn Phe Ser Ile Lys Glu Ile Phe Asp Lys Ala Ile
                 85                  90                  95
Ser Ala Arg Lys Ile Asn Arg Pro Met Leu Gln Ala Ala Leu Met Leu
            100                 105                 110
Arg Lys Lys Gly Phe Thr Thr Ala Ile Leu Thr Asn Thr Trp Leu Asp
            115                 120                 125
Asp Arg Ala Glu Arg Asp Gly Leu Ala Gln Leu Met Cys Glu Leu Lys
 130                     135                 140
Met His Phe Asp Phe Leu Ile Glu Ser Cys Gln Val Gly Met Val Lys
 145                     150                 155                 160
Pro Glu Pro Gln Ile Tyr Lys Phe Leu Leu Asp Thr Leu Lys Ala Ser
                 165                 170                 175
Pro Ser Glu Val Val Phe Leu Asp Asp Ile Gly Ala Asn Leu Lys Pro
            180                 185                 190
Ala Arg Asp Leu Gly Met Val Thr Ile Leu Val Gln Asp Thr Asp Thr
            195                 200                 205
Ala Leu Lys Glu Leu Glu Lys Val Thr Gly Ile Gln Leu Leu Asn Thr
            210                 215                 220
Pro Ala Pro Leu Pro Thr Ser Cys Asn Pro Ser Asp Met Ser His Gly
 225                     230                 235                 240
Tyr Val Thr Val Lys Pro Arg Val Arg Leu His Phe Val Glu Leu Gly
                 245                 250                 255
Trp Pro Ala Val Cys Leu Cys His Gly Phe Pro Glu Ser Trp Tyr Ser
            260                 265                 270
Trp Arg Tyr Gln Ile Pro Ala Leu Ala Gln Ala Gly Tyr Arg Val Leu
            275                 280                 285
Ala Met Asp Met Lys Gly Tyr Gly Glu Ser Ser Ala Pro Pro Glu Ile
 290                     295                 300
Glu Glu Tyr Cys Met Glu Val Leu Cys Lys Glu Met Val Thr Phe Leu
305                  310                 315                 320
Asp Lys Leu Gly Leu Ser Gln Ala Val Phe Ile Gly His Asp Trp Gly
                 325                 330                 335
Gly Met Leu Val Trp Tyr Met Ala Leu Phe Tyr Pro Glu Arg Val Arg
            340                 345                 350
Ala Val Ala Ser Leu Asn Thr Pro Phe Ile Pro Ala Asn Pro Asn Met
            355                 360                 365
Ser Pro Leu Glu Ser Ile Lys Ala Asn Pro Val Phe Asp Tyr Gln Leu
 370                     375                 380
Tyr Phe Gln Glu Pro Gly Val Ala Glu Ala Glu Leu Glu Gln Asn Leu
385                  390                 395                 400
Ser Arg Thr Phe Lys Ser Leu Phe Arg Ala Ser Asp Glu Ser Val Leu
                 405                 410                 415
Ser Met His Lys Val Cys Glu Ala Gly Gly Leu Phe Val Asn Ser Pro
            420                 425                 430
Glu Glu Pro Ser Leu Ser Arg Met Val Thr Glu Glu Ile Gln Phe
            435                 440                 445
```

| | | | | | | | | | | | | |
|---|---|---|---|---|---|---|---|---|---|---|---|---|
| Tyr | Val | Gln | Gln | Phe | Lys | Lys | Ser | Gly | Phe | Arg | Gly | Pro | Leu | Asn | Trp |
| 450 | | | | | 455 | | | | | 460 | | | | | |

Tyr Arg Asn Met Glu Arg Asn Trp Lys Trp Ala Cys Lys Ser Leu Gly
465                 470                 475                 480

Arg Lys Ile Leu Ile Pro Ala Leu Met Val Thr Ala Glu Lys Asp Phe
                485                 490                 495

Val Leu Val Pro Gln Met Ser Gln His Met Glu Asp Trp Ile Pro His
            500                 505                 510

Leu Lys Arg Gly His Ile Glu Asp Cys Gly His Trp Thr Gln Met Asp
            515                 520                 525

Lys Pro Thr Glu Val Asn Gln Ile Leu Ile Lys Trp Leu Asp Ser Asp
530                 535                 540

Ala Arg Asn Pro Pro Val Val Ser Lys Met
545                 550

<210> SEQ ID NO 2
<211> LENGTH: 1665
<212> TYPE: DNA
<213> ORGANISM: Homo sapiens
<220> FEATURE:
<223> OTHER INFORMATION: human soluble epoxide hydrolase (sEH, cytosolic EH)

<400> SEQUENCE: 2

```
atgacgctgc gcggcgccgt cttcgacctt gacggggtgc tggcgctgcc agcggtgttc        60
ggcgtcctcg gccgcacgga ggaggccctg gcgctgccca gggacttct gaatgatgct       120
ttccagaaag ggggaccaga gggtgccact acccggctta tgaaaggaga gatcacactt       180
tcccagtgga taccactcat ggaagaaaac tgcaggaagt gctccgagac cgctaaagtc       240
tgcctcccca agaatttctc cataaaagaa atctttgaca ggcgatttc agccagaaag       300
atcaaccgcc ccatgctcca ggcagctctc atgctcagga gaaaggatt cactactgcc       360
atcctcacca cacctggct ggacgaccgt gctgagagag atggcctggc ccagctgatg       420
tgtgagctga agatgcactt tgacttcctg atagagtcgt gtcaggtggg aatggtcaaa       480
cctgaacctc agatctacaa gtttctgctg acaccctga aggccagccc cagtgaggtc       540
gttttttttgg atgacatcgg ggctaatctg aagccagccc gtgacttggg aatggtcacc       600
atcctggtcc aggacactga cacggccctg aagaactgg agaaagtgac cggaatccag       660
cttctcaata ccccggcccc tctgccgacc tcttgcaatc caagtgacat gagccatggg       720
tacgtgacag taaagcccag ggtccgtctg cattttgtgg agctgggctg gcctgctgtg       780
tgcctctgcc atggatttcc cgagagttgg tattcttgga ggtaccagat ccctgctctg       840
gcccaggcag gttaccgggt cctagctatg gacatgaaag ctatggaga gtcatctgct       900
cctcccgaaa tagaagaata ttgcatggaa gtgttatgta aggagatggt aaccttcctg       960
gataaactgg gcctctctca gcagtgttc attggccatg actggggtgg catgctggtg      1020
tggtacatgg ctctcttcta ccccgagaga gtgagggcgg tggccagttt gaatactccc      1080
ttcataccag caaatcccaa catgtcccct tggagagta caaagccaa cccagtattt      1140
gattaccagc tctacttcca gaaccagga gtggctgagg ctgaactgga acagaacctg      1200
agtcggactt tcaaaagcct cttcagagca agcgatgaga gtgttttatc catgcataaa      1260
gtctgtgaag cgggaggact ttttgtaaat agcccagaag agcccagcct cagcaggatg      1320
gtcactgagg aggaaatcca gttctatgtg cagcagttca gaagtctggg ttcagaggt      1380
cctctaaact ggtaccgaaa catggaaagg aactggaagt gggcttgcaa aagcttggga      1440
```

-continued

```
cggaagatcc tgattccggc cctgatggtc acggcggaga aggacttcgt gctcgttcct    1500
cagatgtccc agcacatgga ggactggatt ccccacctga aaaggggaca cattgaggac    1560
tgtgggcact ggacacagat ggacaagcca accgaggtga atcagatcct cattaagtgg    1620
ctggattctg atgcccggaa cccaccggtg gtctcaaaga tgtag                    1665

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) small
      interfering RNA (siRNA) target sequence

<400> SEQUENCE: 3
cagtgttcat tggccatgac tgg                                             23

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      sense small interfering RNA (siRNA)
<220> FEATURE:
<223> OTHER INFORMATION: Description of Artificial Sequence:human
      soluble epoxide hydrolase (sEH, cytosolic EH) sense small
      interfering RNA (siRNA)

<400> SEQUENCE: 4
guguucauug gccaugacut t                                               21

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      antisense small interfering RNA (siRNA)
<220> FEATURE:
<223> OTHER INFORMATION: Description of Artificial Sequence:human
      soluble epoxide hydrolase (sEH, cytosolic EH) antisense
      small interfering RNA (siRNA)

<400> SEQUENCE: 5
agucauggcc aaugaacact t                                               21

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) small
      interfering RNA (siRNA) target sequence

<400> SEQUENCE: 6
gaaaggctat ggagagtcat ctg                                             23

<210> SEQ ID NO 7
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:human
      soluble epoxide hydrolase (sEH, cytosolic EH)
      sense small interfering RNA (siRNA)
<220> FEATURE:
<223> OTHER INFORMATION: Description of Artificial Sequence:human
      soluble epoxide hydrolase (sEH, cytosolic EH) sense small
      interfering RNA (siRNA)

<400> SEQUENCE: 7
aaggcuaugg agagucauct t                                              21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      antisense small interfering RNA (siRNA)
<220> FEATURE:
<223> OTHER INFORMATION: Description of Artificial Sequence:human
      soluble epoxide hydrolase (sEH, cytosolic EH) antisense
      small interfering RNA (siRNA)

<400> SEQUENCE: 8
gaugacucuc cauagccuut t                                              21

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) small
      interfering RNA (siRNA) target sequence

<400> SEQUENCE: 9
aaaggctatg gagagtcatc tgc                                            23

<210> SEQ ID NO 10
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      sense small interfering RNA (siRNA)
<220> FEATURE:
<223> OTHER INFORMATION: Description of Artificial Sequence:human
      soluble epoxide hydrolase (sEH, cytosolic EH) sense small
      interfering RNA (siRNA)

<400> SEQUENCE: 10
aggcuaugga gagucaucut t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      antisense small interfering RNA (siRNA)
<220> FEATURE:
<223> OTHER INFORMATION: Description of Artificial Sequence:human
      soluble epoxide hydrolase (sEH, cytosolic EH) antisense
      small interfering RNA (siRNA)

<400> SEQUENCE: 11
agaugacucu ccauagccut t                                              21
```

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) small
      interfering RNA (siRNA) target sequence

<400> SEQUENCE: 12
caagcagtgt tcattggcca tga                                              23

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      sense small interfering RNA (siRNA)
<220> FEATURE:
<223> OTHER INFORMATION: Description of Artificial Sequence:human
      soluble epoxide hydrolase (sEH, cytosolic EH) sense small
      interfering RNA (siRNA)

<400> SEQUENCE: 13
agcaguguuc auuggccaut t                                                21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      antisense small interfering RNA (siRNA)
<220> FEATURE:
<223> OTHER INFORMATION: Description of Artificial Sequence:human
      soluble epoxide hydrolase (sEH, cytosolic EH) antisense
      small interfering RNA (siRNA)

<400> SEQUENCE: 14
auggccaaug aacacugcut t                                                21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) small
      interfering RNA (siRNA) target sequence

<400> SEQUENCE: 15
cagcacatgg aggactggat tcc                                              23

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      sense small interfering RNA (siRNA)
<220> FEATURE:
<223> OTHER INFORMATION: Description of Artificial Sequence:human
      soluble epoxide hydrolase (sEH, cytosolic EH) sense small
      interfering RNA (siRNA)

<400> SEQUENCE: 16
gcacauggag gacuggauut t                                                21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:human
      soluble epoxide hydrolase (sEH, cytosolic EH)
      antisense small interfering RNA (siRNA)
<220> FEATURE:
<223> OTHER INFORMATION: Description of Artificial Sequence:human
      soluble epoxide hydrolase (sEH, cytosolic EH) antisense
      small interfering RNA (siRNA)

<400> SEQUENCE: 17
aauccagucc uccaugugct t                                                21

<210> SEQ ID NO 18
<211> LENGTH: 9
<212> TYPE: DNA
<213> ORGANISM: Artificial Sequence
<220> FEATURE:
<223> OTHER INFORMATION: Description of Artificial Sequence:hairpin RNA
      linker section, short spacer

<400> SEQUENCE: 18 ttcaagaga                                                              9

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) target
      sequence

<400> SEQUENCE: 19
cagtgttcat tggccatgac tgg                                              23

<210> SEQ ID NO 20
<211> LENGTH: 59
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) sense strand

<400> SEQUENCE: 20
gatccccgtg ttcattggcc atgactttca agagaagtca tggccaatga acactttt       59

<210> SEQ ID NO 21
<211> LENGTH: 59
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) antisense
      strand

<400> SEQUENCE: 21
agctaaaaag tgttcattgg ccatgacttc tcttgaaagt catggccaat gaacacggg      59

```
<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) target
      sequence

<400> SEQUENCE: 22
gaaaggctat ggagagtcat ctg                                         23

<210> SEQ ID NO 23
<211> LENGTH: 59
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) sense strand

<400> SEQUENCE: 23
gatccccaag gctatggaga gtcatcttca agagagatga ctctccatag cctttttt    59

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) antisense
      strand

<400> SEQUENCE: 24
agctaaaaaa aggctatgga gagtcatctc tcttgaagat gactctccat agccttggg   59

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) target
      sequence

<400> SEQUENCE: 25
aaaggctatg gagagtcatc tgc                                         23

<210> SEQ ID NO 26
<211> LENGTH: 59
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) sense strand

<400> SEQUENCE: 26
gatccccagg ctatggagag tcatctttca agagaagatg actctccata gccttttt    59

<210> SEQ ID NO 27
<211> LENGTH: 59
<212> TYPE: DNA
<213> ORGANISM: Artificial Sequence
<220> FEATURE:
```

<223> OTHER INFORMATION: Description of Artificial Sequence:human
     soluble epoxide hydrolase (sEH, cytosolic EH) short
     hairpin small interfering RNA (siRNA) antisense
     strand

<400> SEQUENCE: 27
agctaaaaaa ggctatggag agtcatcatc tcttgaaaga tgactctcca tagcctggg      59

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence:human
     soluble epoxide hydrolase (sEH, cytosolic EH) short
     hairpin small interfering RNA (siRNA) target
     sequence

<400> SEQUENCE: 28
caagcagtgt tcattggcca tga                                             23

<210> SEQ ID NO 29
<211> LENGTH: 59
<212> TYPE: DNA
<213> ORGANISM: Artificial Sequence
<220> FEATURE:
<223> OTHER INFORMATION: Description of Artificial Sequence:human
     soluble epoxide hydrolase (sEH, cytosolic EH) short
     hairpin small interfering RNA (siRNA) sense strand

<400> SEQUENCE: 29
gatccccagc agtgttcatt ggccatttca agagaatggc caatgaacac tgcttttt      59

<210> SEQ ID NO 30
<211> LENGTH: 59
<212> TYPE: DNA
<213> ORGANISM: Artificial Sequence
<220> FEATURE:
<223> OTHER INFORMATION: Description of Artificial Sequence:human
     soluble epoxide hydrolase (sEH, cytosolic EH) short
     hairpin small interfering RNA (siRNA) antisense
     strand

<400> SEQUENCE: 30
agctaaaaaa gcagtgttca ttggccattc tcttgaaatg ccaatgaac actgctggg      59

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence:human
     soluble epoxide hydrolase (sEH, cytosolic EH) short
     hairpin small interfering RNA (siRNA) target
     sequence

<400> SEQUENCE: 31
cagcacatgg aggactggat tcc                                             23

<210> SEQ ID NO 32
<211> LENGTH: 59
<212> TYPE: DNA
<213> ORGANISM: Artificial Sequence
<220> FEATURE:
<223> OTHER INFORMATION: Description of Artificial Sequence:human
     soluble epoxide hydrolase (sEH, cytosolic EH) short
     hairpin small interfering RNA (siRNA) sense strand

<400> SEQUENCE: 32
gatccccgca catggaggac tggattttca agagaaatcc agtcctccat gtgctttttt    59

<210> SEQ ID NO 33
<211> LENGTH: 59
<212> TYPE: DNA
<213> ORGANISM: Artificial Sequence
<220> FEATURE:
<223> OTHER INFORMATION: Description of Artificial Sequence:human
      soluble epoxide hydrolase (sEH, cytosolic EH) short
      hairpin small interfering RNA (siRNA) antisense
      strand

<400> SEQUENCE: 33
agctaaaaag cacatggagg actggatttc tcttgaaaat ccagtcctcc atgtgcggg    59

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence:human
      soluble epoxide hydrolase (sEH, cytosolic EH) antisense
      sequence

<400> SEQUENCE: 34
uguccagugc ccacaguccu                                                20

<210> SEQ ID NO 35
<211> LENGTH: 20
<212> TYPE: RNA
<213> ORGANISM: Artificial Sequence
<220> FEATURE:
<223> OTHER INFORMATION: Description of Artificial Sequence:human
      soluble epoxide hydrolase (sEH, cytosolic EH) antisense
      sequence

<400> SEQUENCE: 35
uucccaccug acacgacucu                                                20

<210> SEQ ID NO 36
<211> LENGTH: 20
<212> TYPE: RNA
<213> ORGANISM: Artificial Sequence
<220> FEATURE:
<223> OTHER INFORMATION: Description of Artificial Sequence:human
      soluble epoxide hydrolase (sEH, cytosolic EH) antisense
      sequence

<400> SEQUENCE: 36
guucagccuc agccacuccu                                                20

<210> SEQ ID NO 37
<211> LENGTH: 19
<212> TYPE: RNA
<213> ORGANISM: Artificial Sequence
<220> FEATURE:
<223> OTHER INFORMATION: Description of Artificial Sequence:human
      soluble epoxide hydrolase (sEH, cytosolic EH) antisense
      sequence

<400> SEQUENCE: 37
aguccucccg cuucacaga                                                 19

<210> SEQ ID NO 38
<211> LENGTH: 21
<212> TYPE: RNA
<213> ORGANISM: Artificial Sequence

```
-continued

<220> FEATURE:
<223> OTHER INFORMATION: Description of Artificial Sequence:human
      soluble epoxide hydrolase (sEH, cytosolic EH) antisense
      sequence

<400> SEQUENCE: 38
gcccacuucc aguuccuuuc c                                             21
```